(12) United States Patent
Goldsmith et al.

(10) Patent No.: US 9,535,219 B2
(45) Date of Patent: *Jan. 3, 2017

(54) SINGLE MOLECULE SPECTROSCOPY USING PHOTOTHERMAL TUNING OF OPTICAL MICROCAVITIES

(71) Applicant: Wisconsin Alumni Research Foundation, Madison, WI (US)

(72) Inventors: Randall Howard Goldsmith, Madison, WI (US); Kevin Daniel Heylman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/621,502

(22) Filed: Feb. 13, 2015

(65) Prior Publication Data

US 2015/0362425 A1    Dec. 17, 2015

Related U.S. Application Data

(60) Provisional application No. 61/939,964, filed on Feb. 14, 2014.

(51) Int. Cl.
*G02B 6/293* (2006.01)
*G01N 21/17* (2006.01)
(Continued)

(52) U.S. Cl.
CPC ......... *G02B 6/29341* (2013.01); *G01N 21/171* (2013.01); *G01N 21/7746* (2013.01); *G02F 1/0147* (2013.01); *H01S 3/0604* (2013.01)

(58) Field of Classification Search
CPC ........... G01N 21/7746; G01N 21/553–21/554;
G01N 21/63; G01N 21/636; G02B 6/29341; G01J 3/06; G01J 2003/102; G01J 3/42; G01J 2003/423
See application file for complete search history.

(56) References Cited

U.S. PATENT DOCUMENTS 6,521,324 B1    2/2003  Debe et al.
6,633,696 B1   10/2003  Vahala et al.
(Continued)

OTHER PUBLICATIONS

Juejun Hu, Ultra-sensitive chemical vapor detection using microcavity photothermal spectroscopy, Oct. 5, 2010, Optics Express, Vo. 18, No. 21, pp. 1-13.*

(Continued)

*Primary Examiner* — Michael P Lapage
(74) *Attorney, Agent, or Firm* — Bell & Manning, LLC

(57) ABSTRACT

A method comprises exposing the surface of an optical microcavity characterized by at least one resonance frequency to a sample such that a single particle or molecule from the sample adsorbs onto the surface of the microcavity; evanescently coupling a probe laser beam into the microcavity, the wavelength of the probe laser beam substantially matching the at least one resonance frequency; illuminating the surface of the microcavity with a free space pump light beam and moving the focal spot of the free space pump light beam such that the focal spot substantially overlaps with the single particle/molecule; and detecting light from the probe laser beam. The wavelength of the free space pump light beam generates sufficient heat via energy absorbed by the single particle/molecule to induce a shift in the at least one resonance frequency, thereby providing a change in an optical characteristic of the detected light.

20 Claims, 18 Drawing Sheets

(51) Int. Cl.
    *G01N 21/77*    (2006.01)
    *G02F 1/01*     (2006.01)
    *H01S 3/06*     (2006.01)

(56) References Cited

U.S. PATENT DOCUMENTS

| | | | |
|---|---|---|---|
| 6,741,628 | B2 | 5/2004 | Painter et al. |
| 6,777,244 | B2 | 8/2004 | Pepper et al. |
| 7,384,797 | B1 | 6/2008 | Blair |
| 7,781,217 | B2 | 8/2010 | Armani et al. |
| 8,597,577 | B2 | 12/2013 | Flagan et al. |
| 8,957,445 | B2 | 2/2015 | Senellart et al. |
| 2001/0004411 | A1* | 6/2001 | Yariv ............ B82Y 20/00 385/28 |
| 2008/0089367 | A1* | 4/2008 | Srinivasan ....... B82Y 20/00 372/19 |
| 2009/0237666 | A1* | 9/2009 | Vollmer .......... G01N 21/77 356/432 |
| 2010/0085573 | A1* | 4/2010 | Lu .............. G01N 21/7746 356/480 |
| 2011/0139970 | A1* | 6/2011 | He ............. G01N 21/7746 250/227.18 |
| 2014/0193155 | A1* | 7/2014 | Popovic ......... H04J 14/02 398/82 |
| 2014/0290370 | A1 | 10/2014 | Hossein-Zadeh |
| 2015/0234211 | A1 | 8/2015 | Goldsmith et al. |

OTHER PUBLICATIONS

Arbouet et al., Direct Measurement of the Single-Metal-Cluster Optical Absorption, Physical Review Letters, vol. 93, No. 12, Sep. 14, 2004, pp. 127401-1-127401-4.

Rokhsari et al., Ultralow Loss, High Q, Four Port Resonant Couplers for Quantum Optics and Photonics, Physical Review Letters, vol. 92, No. 25, Jun. 25, 2004, pp. 253905-1-253905-4.

Tapalian et al., Thermooptical Switches Using Coated Microsphere Resonators, IEEE Photonics Technology Letters, vol. 14, No. 8, Aug. 2002, pp. 1118-1120.

Pan et al., Aligning microcavity resonances in silicon photonic-crystal slabs using laser-pumped thermal tuning, Applied Physics Letters, vol. 92, No. 103114, Mar. 12, 2008, pp. 1-3.

Topolancik et al., Photoinduced Transformations in Bacteriorhodopsin Membrane Monitored with Optical Microcavities, Biophysical Journal, vol. 92, Mar. 2007, pp. 2223-2229.

Armani et al., Label-Free, Single-Molecule Detection with Optical Microcavities, Science, vol. 317, Aug. 10, 2007, pp. 783-787.

Benson et al., Micro-Optical Resonators for Microlasers and Integrated Optoelectronics: Recent advances and future challenges, Frontiers of Planar Lightwave Circuit Technology: Design, Simulation and Fabrication, 2005, pp. 39-70.

Yoshie et al., Optical Microcavity: Sensing down to Single Molecules and Atoms, Sensors, vol. 11, Feb. 7, 2011, pp. 1972-1991.

Righini et al., Whispering gallery mode microresonators: Fundamentals and applications, Rivista Del Nuovo Cimento, vol. 34, No. 7, 2011, pp. 435-488.

Heylman et al., Photothermal mapping and free-space laser tuning of toroidal optical microcavities, Applied Physics Letters, vol. 103, No. 211116, Nov. 21, 2013, pp. 1-4.

Heylman et al., Single-Molecule Absorption Spectroscopy Using Toroidal Optical Microcavities, presentation, UW Madison, May 2013.

Heylman et al., Photothermal Microscopy of Nonluminescent Single Particles Enabled by Optical Microresonators, J. Phys. Chem. Lett. 5 (11), May 16, 2014, pp. 1917-1923.

* cited by examiner

SINGLE MOLECULE SPECTROSCOPY USING PHOTOTHERMAL TUNING OF OPTICAL MICROCAVITIES

CROSS-REFERENCE TO RELATED APPLICATIONS

The present application claims priority to U.S. Provisional Patent Application No. 61/939,964 that was filed Feb. 14, 2014, the entire contents of which is hereby incorporated by reference.

REFERENCE TO GOVERNMENT RIGHTS

This invention was made with government support under N66001-12-1-4215 awarded by the US Navy. The government has certain rights in the invention.

BACKGROUND

Whispering-Gallery Mode (WGM) optical microresonators have emerged as rich experimental platforms for quantum optics, photonics, and sensing. In such systems, propagating light is confined to a microstructure and made to repeatedly probe the same volume. Scrupulous minimization of attenuation and scattering translates into tremendously high quality (Q) factors, exceeding $10^{10}$ for microsphere resonators. (See Gorodetsky, M. L.; Savchenkov, A. A.; Ilchenko, V. S.: Ultimate Q of optical microsphere resonators. *Opt. Lett.* 1996, 21, 453-455.) Simultaneously, the propagating mode may be evanescently coupled to the microstructure's immediate environment, leading to repeated interaction with this environment similar to cavity ring-down spectroscopy, though on a substantially smaller length scale. The result is a highly sensitive probe of local environment. Microresonators are also sensitive to the presence of absorbers, and even sensitive in a label-free capacity to the presence of non-absorbing analyte species through differences in the real part of the complex refractive index between the analyte and the surrounding medium (termed the "reactive mechanism"). In particular, toroidal microresonators possess the highest ratio of Q to propagating mode volume. (See Armani, D. K.; Kippenberg, T. J.; Spillane, S. M.; Vahala, K. J.: Ultra-high-Q toroid microcavity on a chip. *Nature* 2003, 421, 925-928 and Kippenberg, T. J.; Spillane, S. M.; Vahala, K. J.: Demonstration of ultra-high-Q small mode volume toroid microcavities on a chip. *Appl. Phys. Lett.* 2004, 85, 6113-6115.) This combination has made them particularly suited for applications in nonlinear optics.

In previous single-particle detection experiments, the reactive mechanism shifts the resonance position upon analyte binding. Though the shift is small, it is resolvable due to the narrowness of the linewidth itself. Various methods have been applied to stabilize the optical properties of the resonator, eliminate drift, or use internal standards to minimize spurious resonance position fluctuations in attempt to increase the resolution and decrease the minimum detectable object size. However, even with these improvements, typical detectable objects are in the ~10-100 nm size range, such as nanoparticles and virus particles. (See Zhu, J. G.; Ozdemir, S. K.; Xiao, Y. F.; Li, L.; He, L. N.; Chen, D. R.; Yang, L.: On-chip single nanoparticle detection and sizing by mode splitting in an ultrahigh-Q microresonator. *Nature Photon.* 2010, 4, 122-122; Lu, T.; Lee, H.; Chen, T.; Herchak, S.; Kim, J. H.; Fraser, S. E.; Flagan, R. C.; Vahala, K.: High sensitivity nanoparticle detection using optical microcavities. *Proc. Natl. Acad. Sci. U.S.A* 2011, 108, 5976-5979; He, L. N.; Ozdemir, K.; Zhu, J. G.; Kim, W.; Yang, L.: Detecting single viruses and nanoparticles using whispering gallery microlasers. *Nature Nanotech.* 2011, 6, 428-432; and Vollmer, F.; Arnold, S.; Keng, D.: Single virus detection from the reactive shift of a whispering-gallery mode. *Proc. Natl. Acad. Sci. U.S.A* 2008, 105, 20701-20704.) Additionally, no chemical information regarding the identity of the adsorbed species is obtained.

SUMMARY

Provided are methods for tuning the resonance frequencies of optical microcavities, applications for the tuning methods (including single molecule spectroscopy), and apparatuses for carrying out the methods and applications.

In one aspect, a method comprises exposing the surface of an optical microcavity characterized by at least one resonance frequency to a sample such that a single particle or a single molecule from the sample adsorbs onto the surface of the microcavity; evanescently coupling a probe laser beam into the microcavity, wherein the wavelength of the probe laser beam substantially matches the at least one resonance frequency; illuminating the surface of the microcavity with a free space pump light beam such that the focal spot of the free space pump light beam substantially overlaps with the single particle or the single molecule; and detecting light from the probe laser beam, wherein the wavelength of the free space pump light beam is that which generates sufficient heat via energy absorbed by the single particle or the single molecule from the free space pump light beam to induce a shift in the at least one resonance frequency, thereby providing a change in an optical characteristic of the detected light from the probe laser beam.

In one aspect, an apparatus for single particle or single molecule spectroscopy comprises, an optical microcavity characterized by at least one resonance frequency; optical components configured to evanescently couple a probe laser beam into the microcavity; optical components configured to illuminate the surface of the microcavity with a free space pump light beam and to move the focal spot of the free space pump light beam across the surface of the microcavity; a detector configured to detect light from the probe laser beam; and a Pound-Drever-Hall servo loop coupled to the probe laser beam, the loop configured to adjust the wavelength of the probe laser beam such that it remains substantially resonant with the microcavity, wherein the apparatus is configured to detect a change in an optical characteristic of the detected light due to a shift in the at least one resonance frequency induced by heat generated and transferred to the microcavity from a single particle or a single molecule in a sample adsorbed on the surface of the microcavity via energy absorbed by the single particle or the single molecule from the free space pump light beam.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
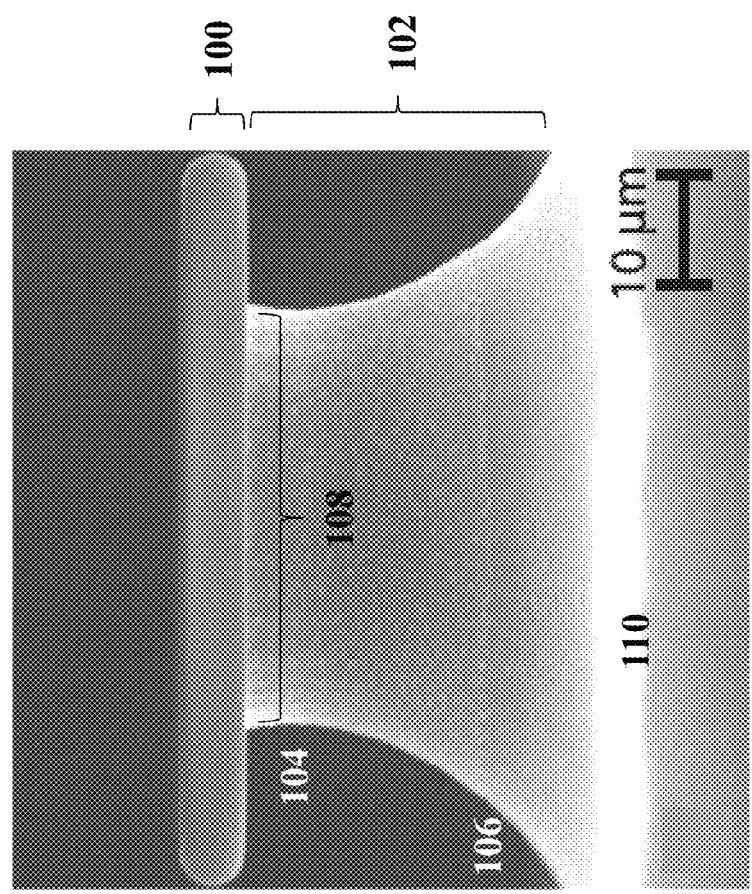
FIG. 1 shows a scanning electron microscope (SEM) image of a whispering gallery mode (WGM) microcavity configured as a toroid (standard toroid) in thermal contact with an absorber element configured as a pillar according to an illustrative embodiment.

Provided are methods for tuning the resonance frequencies of optical microcavities, applications for the tuning methods (including single molecule spectroscopy) and apparatuses for carrying out the methods and applications.

Resonance Tuning Methods

In one aspect, a method is provided which comprises evanescently coupling a probe laser beam into an optical microcavity, the microcavity characterized by at least one resonance frequency and illuminating an absorber element in thermal contact with the microcavity with a free space pump laser beam, whereby heat generated via energy absorbed by the absorber element from the free space pump laser beam is transferred to the microcavity to induce a shift in at least one resonance frequency. The phrase "at least one resonance frequency" encompasses an embodiment in which all the resonance frequencies of the microcavity are shifted.

A variety of optical microcavities may be used. In some embodiments, the optical microcavity is a whispering gallery mode (WGM) optical microcavity, a microcavity which is capable of supporting whispering gallery modes, electromagnetic waves which propagate at the edge of the microcavity. A microcavity may be characterized by its resonance frequencies, those frequencies at which light can be most strongly coupled into and propagate in the microcavity. A microcavity may be characterized by its quality factor, Q, which equals $\lambda/\Delta\lambda$, where $\lambda$ is the wavelength at which a resonance occurs and $\Delta\lambda$ is the linewidth of the resonance at the resonant wavelength. The microcavities may assume a variety of shapes and dimensions and may be formed from a variety of transparent materials, depending upon the desired characteristic, e.g., resonance frequencies, quality factor, etc. By transparent it is meant that the material is substantially transparent at the resonance frequency or frequencies of the microcavity. Suitable exemplary shapes include a sphere, a cylinder, a toroid, a disk or a bottle. Suitable exemplary transparent materials include a variety of semiconductors, glasses and crystals, e.g., GaAs, silicon, silica, $CaF_2$, $MgF_2$ or $LiNbO_3$. In some embodiments, the microcavity is characterized by a Q of at least about $10^7$. This includes embodiments in which the microcavity is characterized by a Q of at least about $10^8$, at least about $10^9$, or at least about $10^{10}$. In some embodiments, the microcavity is uncoated, by which it is meant that the surface of the microcavity is substantially free of a coating material, e.g., a layer of a polymer, a layer of a biological material, a layer of silica, etc.

The absorber element is in thermal contact with the optical microcavity. The absorber element may be configured to absorb energy from the free space pump laser beam, thereby generating heat, and to transfer the heat to the microcavity, thereby inducing a shift in at least one resonance frequency of the microcavity. Suitable configurations include a variety of geometries and dimensions selected to achieve a particular shift in the resonance frequency of the microcavity and/or a particular resonance tuning property (e.g., tuning ratio or switching speed, which are further described below). In particular, the shape and dimensions may be selected to achieve a desired temperature increase of the microcavity, a desired rate of transfer of heat to the microcavity, and/or a desired thermal equilibration time of the microcavity. A suitable exemplary shape of the absorber element is a pillar forming an interfacial region with the microcavity at one of the ends of the pillar. The other end of the pillar may form an interfacial region with an underlying substrate. The pillar may be characterized by a width, which may be taken as the smallest dimension across the interfacial region between the pillar and the microcavity. If the shape of this interfacial region (which is not particularly limited) is circular, the width may be referred to as a diameter. The pillar may also be characterized by the area of the interfacial region between the microcavity and one of the ends of the pillar. The pillar may further be characterized by a height, taken as the dimension along an axis perpendicular to the interface with the microcavity. The dimensions of the pillar at the interface with the microcavity may be different from the dimensions of the pillar at its opposing end. (See FIGS. 1 and 2, further described below.) However, pillars having uniform dimensions along their heights may also be used. Example 1, below, describes how the shape and dimensions of a pillar, including the diameter of a pillar, can be adjusted to achieve a particular temperature increase of the microcavity, rate of heat transfer to the microcavity and thermal equilibration time of the microcavity and therefore, a particular resonance shift, tuning ratio and switching speed.

In some embodiments, the width of the pillar is no more than about 20 μm. This includes embodiments in which the width of the pillar is no more than about 15 μm, no more than about 10 μm, no more than about 5 μm, or no more than about 2 μm. In some embodiments, the width of the pillar is in the range of from about 1 μm to about 50 μm. This includes embodiments in which the width of the pillar is in the range of from about 10 μm to about 40 μm or from about 20 μm to about 40 μm, or from about 25 μm to about 35 μm. In some embodiments, the area of the interfacial region between the pillar and the microcavity is no more than about 300 μm². This includes embodiments in which the area is no more than about 175 μm², no more than about 80 μm², no more than about 20 μm², or no more than about 3 μm². In some embodiments, the area of the interfacial region between the pillar and the microcavity is in the range of from about 1 μm² to about 2000 μm². This includes embodiments in which the area is in the range of from about 80 μm² to about 1250 μm² or from about 300 μm² to about 1250 μm², or from about 500 μm² to about 1000 μm².

The absorber element may be configured from a variety of materials. Typically, the absorber element is composed of a material which is different from the material of the microcavity. The absorber element is desirably composed of a material having a sufficiently high absorption coefficient at the selected wavelength of the free space pump laser beam in order to maximize absorption from the free space pump laser beam. The absorber element may be composed of a material having a sufficiently low absorption coefficient at the selected wavelength of the probe laser beam to minimize absorption from the probe laser beam. For example, the absorber element may be composed of a material which is substantially transparent at the selected wavelength of the probe laser beam. However, since the geometry of the absorber element may be adjusted to minimize or prevent physical contact with the propagating mode in the microcavity, thereby minimizing absorption from this mode, materials which would otherwise absorb some energy from the probe laser beam may be used. The absorber element may be composed of a material having a sufficiently high thermal conductivity in order to maximize heat transfer to the microcavity. Suitable exemplary materials for the absorber include silicon, GaAs, germanium and colored polymers. Colored polymers include, e.g., conjugated polymers or transparent polymers impregnated with dye molecules. Suitable exemplary colored polymers include polyaniline in the emeraldine and pernigraniline forms (deprotonated and half-deprotonated); P3HT (poly(3-hexyl)thiophene); and reduced PEDOT (poly(3,4-ethylenedioxythiophene)).

In some embodiments, the disclosed absorber elements may be distinguished from coating materials, e.g., a layer of a polymer, a layer of a biological material, a layer of silica, etc., which have been deposited on the surface of the microcavity. Thus, in some embodiments, the absorber element is not a coating material which has been deposited on the surface of the micro cavity.

Figure 2:
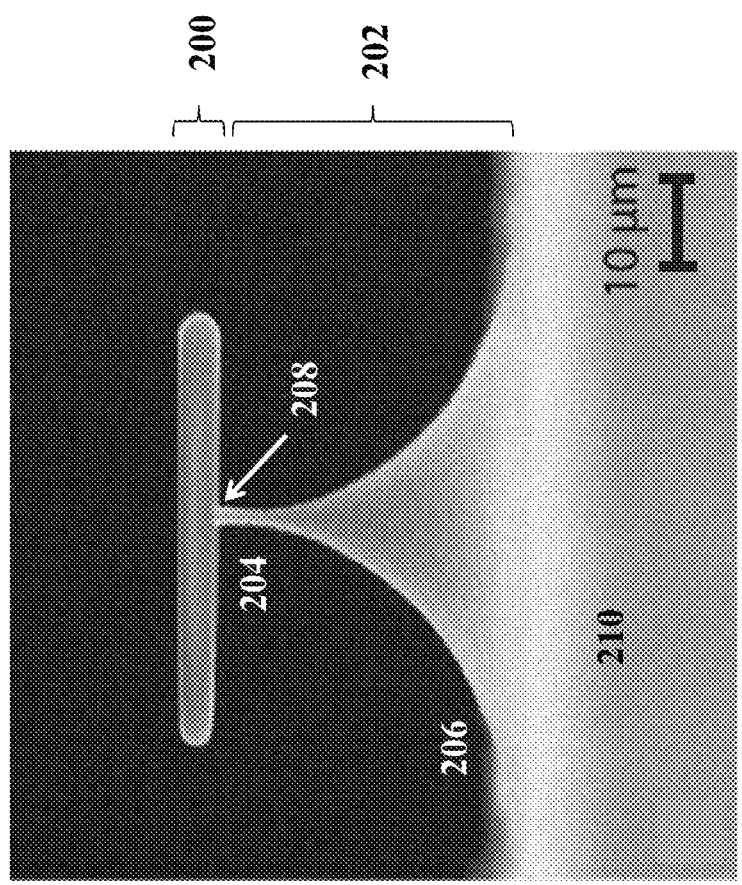
FIG. 2 shows a SEM image of a WGM microcavity configured as a toroid (re-etched toroid) in thermal contact with an absorber element configured as a pillar according to an illustrative embodiment.

FIGS. 1 and 2 show SEM images of WGM optical microcavities (100, 200) configured as a toroid in thermal contact with an absorber element (102, 202) configured as a pillar. The pillars have opposing ends (104, 106, 204, 206), with one end forming an interface (108, 208) with the microcavity (100, 200) and the other end merging with an underlying substrate (110, 210). The diameter of the pillar at the interface 108 is about 30 μm and the diameter of the pillar at the interface 208 is about 2 μm. In these embodiments, the dimensions of the pillar at the interface (108, 208) with the microcavity are different from the dimensions of the pillar at its opposing end (106, 206) as it merges into the underlying substrate (110, 210).

A probe laser beam is evanescently coupled into the optical microcavity. The selected wavelength of the probe laser beam generally depends upon the particular microcavity, which is characterized by resonance frequencies as described above. The selected wavelength of the probe laser beam can be that which substantially matches at least one resonance frequency of the microcavity, i.e., the wavelength can be substantially resonant with the microcavity. However, because the disclosed tuning methods allow for tuning of the microcavity's resonance frequencies, the selected wavelength of the probe laser beam need not match one of the microcavity's intrinsic resonance frequencies. The wavelength of the probe laser beam may be fixed or may be tuned (i.e., scanned) over a range of wavelengths. The probe laser beam may be evanescently coupled into the optical microcavity via a variety of techniques. A suitable technique is evanescent coupling via a tapered optical fiber.

A free space pump laser beam illuminates the absorber element. The free space pump laser beam can be delivered to the absorber element via a variety of techniques and optical components. However, by "free space" it is meant that the pump laser beam is not delivered to the absorber element via the propagating mode of the microcavity. A free space pump laser beam is one which is not evanescently coupled to the microcavity via the propagating mode. As further described below, a variety of optical components may be used to illuminate the absorber element with a free space pump laser beam, including microscope objectives, lens-tipped fiber optics or scanning microscopy tips. Thus, a free space pump laser beam can include beams which are delivered to the absorber element via a near-field interaction. The selected wavelength of the free space pump laser beam generally depends upon the particular absorber element. The selected wavelength of the free space pump laser beam can be that which achieves a desired amount of absorption of energy, e.g., maximal absorption, by the absorber element. Since the free space pump laser beam is not delivered to the absorber element via the propagating mode of the microcavity, the selected wavelength of the free space pump laser beam need not be a wavelength which matches a resonance frequency of the microcavity. Thus, the selected wavelength may be substantially non-resonant with the microcavity. However, wavelengths which are resonant with the microcavity may also be used. The wavelength of the free space pump laser beam may be fixed or may be tuned (i.e., scanned) over a range of wavelengths. Since the free space pump laser beam is not delivered to the absorber element via the propagating mode of the microcavity, a broad range of wavelengths may be used.

The free space pump laser beam may be characterized by an intensity, which may be adjusted by adjusting the power of the laser beam and/or the focal spot size of the laser beam. Different intensities may be used, e.g., the intensity can be selected to achieve a desired shift in the resonance frequency of the microcavity. In some embodiments, the diameter of the focal spot of the free space pump laser substantially matches the width of an absorber element configured as a pillar. In some embodiments, the ratio of the diameter of the microcavity to the diameter of the focal spot size of the free space pump laser beam is at least about 10. This includes embodiments in which the ratio is at least about 20 or at least about 30. In some embodiments, the free space pump laser beam is focused to a diffraction-limited focal spot. The position of the free space pump laser beam may be defined as the position of its focal spot with respect to the propagating mode in the microcavity. In some embodiments, the focal spot does not substantially overlap with the propagating mode in the microcavity.

In another aspect, an apparatus is provided which comprises an optical microcavity, the microcavity characterized by at least one resonance frequency; optical components configured to evanescently couple a probe laser beam into the microcavity; an absorber element in thermal contact with the microcavity; and optical components configured to illuminate the absorber element with a free space pump laser beam, wherein the absorber element is configured to absorb energy from the free space pump laser beam, thereby generating heat, and to transfer the heat to the microcavity, thereby inducing a shift in the at least one resonance frequency.

A variety of optical components may be associated with the probe laser beam, including optical components configured to receive the probe laser beam, to direct it towards the microcavity and to evanescently couple it into the microcavity (e.g., tapered optical fiber). Similarly, a variety of optical components may be associated with a pump laser beam, including optical components configured to receive a pump laser beam, direct it towards the absorber element and to deliver it or focus it onto the absorber element. For example, microscope objectives, lens-tipped fiber optics or scanning microscopy tips may be used to focus a pump laser beam onto the absorber element. These exemplary optical components do not deliver the pump laser beam to the absorber element via the propagating mode of the microcavity and thus, provide for illumination of the absorber element with a "free space pump laser beam." Other optical components associated with the pump laser beam can include gimbal-mounted mirrors and relay optics to control the position of the focal spot of the free space pump laser beam with respect to the microcavity and the absorber element. The apparatus may comprise additional optical components typically used for manipulating laser beams, e.g., components for phase modulation, amplitude modulation and polarization control. The apparatus may comprise components configured to lock the probe laser beam to a resonance frequency of the microcavity via the Pound-Drever-Hall (PDH) technique. If a tapered optical fiber is used to evanescently couple the probe laser beam into the microcavity, the apparatus may comprise a piezo-positioning system to align the tapered optical fiber with the microcavity.

The apparatus may further comprise light sources (e.g., light emitting diodes (LEDs) or lasers) configured to generate the probe laser beam and the free space pump laser beam. In some embodiments of the disclosed methods and apparatuses, non-laser light sources may be used such that the term "laser beam" as used herein can be replaced with the term "light beam," i.e., a light beam from a non-laser light source. However, in other embodiments, the light source(s) are configured to generate true laser beams. The apparatus may further comprise a detector configured to detect light from the probe laser beam transmitted through the microcavity. The detector may be configured to provide as output, the power of the transmitted light. The apparatus may further comprise multiple evanescently coupled waveguides configured to allow photothermal switching between multiple probe wavelengths. For example, the apparatus may further comprise optical components configured to evanescently couple multiple probe laser beams having different wavelengths into the microcavity. Using the disclosed tuning methods, the free space pump laser beam can be used to tune the resonance frequency of the microcavity and to switch between these different wavelengths, i.e., to select which of the different wavelengths is resonant with the microcavity. The apparatus may comprise an array of optical microcavities, each microcavity in thermal contact with an absorber element. Each of the microcavities in the array may be independently tuned using the disclosed methods. As such, the apparatus may further comprise microlenses to focus multiple independently controlled free space pump laser beams onto multiple microcavities.

The apparatuses may be characterized by resonance tuning properties, including tuning ratio and switching speed. Tuning ratio provides a measure of the magnitude of the shift of resonance frequency that can be achieved at a particular power of the free space pump laser beam. In some embodiments, the tuning ratio is at least about 3000 fm/mW. This includes embodiments in which the tuning ratio is at least about 5000 fm/mW, at least about $1\times10^4$ fm/mW, at least about $1.5\times10^4$ fm/mW, at least about $1\times10^5$ fm/mW, at least about $1.5\times10^5$ fm/mW, or at least about $2\times10^5$ fm/mW. Switching speed provides a measure of how fast a particular shift of resonance frequency may be achieved. In some embodiments, the switching speed is at least about 350 Hz. This includes embodiments in which the switching speed is at least about 500 Hz, at least about 1 kHz, at least about 2 kHz, at least about 4 kHz, at least about 5 kHz, at least about 100 kHz, at least about 250 kHz, or at least about 500 kHz. These switching speeds can refer to the switching speed measured at a particular power of the free space pump laser beam (e.g., 1 µW or 1 mW). These switching speeds can also refer to the switching speed measured for a particular resonance shift (e.g., no more than 30 linewidths or no more than 7 linewidths). The apparatus may further comprise a cooling element in thermal contact with the microcavity configured to cool the microcavity after the temperature of the microcavity has increased due to heat transferred to it from the absorber element. A suitable exemplary cooling element is a body of liquid in contact with the surface of the microcavity. The cooling element may increase the cooling rate of the microcavity such that a higher switching speed can be obtained as compared to the apparatus without the cooling element for a given power of the free space pump laser beam.

The resonance tuning methods and apparatuses for carrying out the resonance tuning methods will find use in a variety of optoelectronic applications and devices, including optical switching. For an optical switching application, additional components may be included in the apparatus as described in H. Rokhsari and K. J. Vahala, "Ultralow Loss, High Q, Four Port Resonant Couplers for Quantum Optics and Photonics," *Physical Review Letters*, Vol. 92, No. 25, Jun. 25, 2004.

Single Particle and Single Molecule Spectroscopy

The resonance tuning methods will also find use in single particle and single molecule spectroscopy. In such spectroscopic methods, the absorber element is a single particle or a single molecule. Upon illumination with the free space pump laser beam, the single particle or single molecule absorbs energy from the free space pump laser beam, thereby generating heat, and transfers the heat to the microcavity, thereby inducing a shift in at least one resonance frequency of the microcavity. The spectroscopic methods and apparatuses for carrying out the methods will find use in a variety of applications, including biological and chemical sensing, characterization of thin films and elucidation of chemical reaction kinetics and dynamics.

In one aspect, a method for single particle or single molecule spectroscopy is provided which comprises exposing the surface of an optical microcavity characterized by at least one resonance frequency to a sample; evanescently coupling a probe laser beam into the microcavity; illuminating the surface of the microcavity with a free space pump laser beam such that the focal spot of the free space pump laser beam substantially overlaps with the single particle or single molecule; and detecting light from the probe laser beam, whereby heat generated via energy absorbed by a single particle or a single molecule in the sample from the free space pump laser beam is transferred to the microcavity to induce a shift in the at least one resonance frequency, thereby providing a change in an optical characteristic (e.g., intensity or power) of the detected light from the probe laser beam. Light from the probe laser beam that has been transmitted through the microcavity or back-scattered from the microcavity may be detected.

Any of the optical microcavities described above with respect to the resonance tuning methods may be used. For purposes of this disclosure, optical microcavities are structures which trap light in small volumes by the mechanism of total internal reflection of light at the interface between a transparent material and the surrounding medium (e.g., air); or structures which trap light in small volumes by the mechanism of distributed Bragg reflection from periodical structures in the microcavity; or other optical microcavities derived from periodic arrays. Exemplary suitable optical microcavities include whispering gallery mode optical microcavities, photonic crystal microcavities, optical pillar microcavities and Fabry Perot microcavities.

The microcavities may be configured such that they do not contain materials, or are not in thermal contact with materials, that contribute to background signal via absorption of energy from the free space pump laser beam. In some embodiments, the microcavity is substantially free of silicon. In some embodiments, the microcavity is not in thermal contact with silicon, e.g., a component composed of, or comprising, silicon. In some embodiments, the microcavity (e.g., a silica toroid) has been removed from the growth substrate (e.g., a silicon substrate) upon which it was formed. Such microcavities may be subsequently transferred to a transparent host substrate.

Microcavities may be separated from their growth substrates through the application of pressure from a Tungsten microprobe and subsequently placed onto a transparent host substrate. Other techniques entail the use of epoxy on the tip of an optical fiber and the use of a microfabricated microfork. (See Hossein-Zadeh, M.; Vahala, K. J.: Free ultrahigh-Q microtoroid: a tool for designing photonic devices. *Opt. Express* 2007, 15, 166-175. Peng, B. and Ozdemir, S. K.; Zhu, J. G.; Yang, L.: Photonic molecules formed by coupled hybrid resonators. *Opt. Lett.* 2012, 37, 3435-3437.)

A variety of materials may be used for the transparent host substrate, provided the transparent host substrate is substantially transparent to the free space pump laser beam. Glass is an exemplary suitable transparent host substrate. Thus, in some embodiments, the microcavity overlies a transparent host substrate.

In some embodiments, the surface of the microcavity is coated with a high refractive index polymer. Such coatings may be useful if the microcavity is immersed in water (e.g., for analysis of liquid samples) instead of air. As described in Example 2 below, the resonance shift from a single molecule may decrease upon immersion in a liquid solvent, due to the solvent's greater heat capacity and thermal conductivity than in air. Coating the surface of the microcavity with a high refractive index polymer may help compensate for this decrease. Suitable high refractive index polymers include polymethyl methacrylate. (See Choi, H. S.; Zhang, X. M.; Armani, A. M.: Hybrid silica-polymer ultra-high-Q microresonators. *Opt. Lett.* 2010, 35, 459-461.)

The surface of the optical microcavity is exposed to a sample comprising (or consisting of) single particles or single molecules such that the single particles/molecules contact (e.g., through adsorption or chemical bonding) the surface of the microcavity. Single molecules are typically individual chemical molecules, e.g., an organometallic compound, a polymer molecule, a protein, etc. Single particles typically comprise more than one single molecule, e.g., a polymer domain, a virus particle, etc. Single particles may also include a collection of atoms, e.g., a gold nanocrystal or a nanoparticle, a carbon nanotube or nanofiber.

Single particles and single molecules may be distinguished by their size. Single molecules may be characterized by a size of about 10 nm or less. Single particles may be characterized as objects having at least one dimension in the range of from about 10 nm to about 500 nm. This includes sizes in the range of from about 10 nm to about 250 nm, from about 10 nm to about 100 nm, from about 10 nm to about 75 nm, from about 10 to about 50 nm, or from about 10 nm to about 25 nm.

Exemplary samples which may be studied using the disclosed spectroscopic methods include thin films of organic or inorganic molecules or polymers which have been deposited onto the surface of the microcavity. Detectable single particles may include structural domains formed by a collection of the individual molecules or polymers. Detectable single molecules may include the individual molecules or polymers themselves. Other exemplary samples include liquid samples comprising single particles or single molecules.

Single particles/molecules may be specifically or non-specifically adsorbed onto the surface of the microcavity using known techniques. As further described below, both the liquid samples and the microcavity may be contained within a sample cell. The samples may be configured such that the surface coverage of the single particles/molecules on the microcavity is that which provides for the illumination of no more than about one single particle/molecule by the focal spot of the free space pump laser beam.

The single particles/molecules need not be fluorescent at the selected wavelength(s) of the free space pump laser beam, i.e., they may be substantially non-fluorescent. The single particles/molecules referred to herein may be "target" single particles/molecules in that their existence in a particular sample may be initially unknown.

A probe laser beam is evanescently coupled into the optical microcavity as described above with respect to the resonance tuning methods. The selected wavelength of the probe laser beam is typically not a wavelength which is resonant with a particular transition, e.g., an electronic transition, of the single particle or single molecule. That is, the selected wavelength typically is substantially non-resonant with the single particle or single molecule.

A free space pump laser beam illuminates the surface of the optical microcavity such that the focal spot of the free space pump laser beam substantially overlaps with the single particle or single molecule to be studied. The term "free space" has been defined above with respect to the resonance tuning methods. Heat dissipated from single particles or single molecules which are sufficiently near the propagating mode in the optical microcavity (e.g., substantially near the rim of a toroid microresonator) is capable of shifting the resonance frequencies of the optical microcavity. Thus, the focal spot of the free space pump laser beam may be positioned such that it illuminates an area on the surface of the optical microcavity which substantially overlaps with the propagating mode of the optical microcavity.

The selected wavelength of the free space pump laser beam generally depends upon the single particle or single molecule to be detected in the sample. The selected wavelength of the free space pump laser beam can be that which is substantially resonant with a particular transition of the single particle or single molecule. A variety of transitions (e.g., electronic or vibrational transitions) may be used provided the transition results in an amount of heat sufficient to induce a detectable shift in the resonance frequencies of the microcavity. The selected wavelength of the free space pump laser beam need not be a wavelength which matches a resonance frequency of the microcavity, i.e., the selected wavelength may be substantially non-resonant with the microcavity. The wavelength of the free space pump laser beam may be fixed or may be tuned (i.e., scanned) over a range of wavelengths. If the wavelength is scanned, the range of wavelengths may be selected to encompass the wavelength which is resonant with a particular transition of the single particle or single molecule.

Suitable wavelengths include those in the visible portion of the electromagnetic spectrum, the near-infrared portion of the electromagnetic spectrum and the infrared portion of the electromagnetic spectrum. Suitable wavelengths include wavelengths in the range from about 400 nm to about 1650 nm and those in the range of from about 2 μm to about 20 μm. In some embodiments, the range of wavelengths over which the free space pump laser beam is scanned is greater than the free spectral range (FSR) of the microcavity.

The free space pump laser beam may be characterized by an intensity, which may be adjusted by adjusting the power of the laser beam and/or the focal spot size of the laser beam. Different intensities may be used. However, to minimize background signal, the intensity can be selected to be sufficiently below the saturation intensity of the single particle or single molecule at the selected wavelength of the free space pump laser beam, as further described in Example 2, below. Other characteristics of the free space pump laser beam, e.g., the focal spot size, may be as described above with respect to the resonance tuning methods.

The disclosed spectroscopic methods may be used to determine the presence of a single particle or single molecule by detecting a change in an optical characteristic of the detected light from the probe laser beam induced by the single particle/molecule. However, the disclosed spectroscopic methods may also be used to obtain absorption spectra (e.g., electronic or vibrational absorption spectra) of single particles and single molecules, thereby providing identification of the single particle/molecule via its spectral fingerprint as well as information about the structure and properties of the single particle/molecule.

In one embodiment, the wavelength of the probe laser beam is substantially resonant with the microcavity and the wavelength of the free space pump laser beam is scanned over a range of wavelengths encompassing a wavelength which is resonant with a transition (e.g., an electronic or vibrational transition) of the single particle or single molecule. As the free space pump laser beam is scanned in wavelength, different amounts of heat will be dissipated to the microcavity as a function of the single particle/molecule's wavelength-dependent extinction coefficient, yielding different magnitudes of cavity-resonance shift and thus, changes in an optical characteristic (e.g., changes in intensity or power) of light detected from the probe laser beam. Detecting the light from the probe laser beam (e.g., the transmitted or back-scattered light) as a function of the wavelength of the free space pump laser beam yields the absorption spectrum of the single particle or single molecule. In this embodiment, instead of scanning the wavelength of the free space pump laser beam over a range of wavelengths, multiple light sources configured to generate multiple pump laser beams having different wavelengths may be used. The pump laser beam-wavelength-dependent response yields the absorption spectrum.

The disclosed spectroscopic methods may also be used to follow the real-time dynamics of single particles and single molecules. For example, the methods may be used to follow an organometallic compound as it catalyzes a chemical reaction and transitions from an initial state, to an intermediate state(s) and to a final state.

In one embodiment, the wavelength of the probe laser beam is substantially resonant with the microcavity. The wavelength of the free space pump laser beam may be selected to be substantially near an absorption maximum of a transition (e.g., an electronic transition) of a particular state of the single particle or single molecule (e.g., the initial state of the organometallic compound in the chemical reaction catalyzed by the compound). The wavelength of the free space pump laser beam may be, but need not be, substantially resonant with one of these transitions. Light from the probe laser beam (e.g., light transmitted through the microcavity or back-scattered from the microcavity) is detected for a period of time. A particular optical characteristic (e.g., intensity or power value) of the detected light at a particular point in time may be associated with a particular state of the single particle or single molecule. The number of discrete values of the optical characteristic provides information about the number of states the single particle/molecule occupies over the period of time (e.g., the number of intermediate states of the organometallic compound as it catalyzes the chemical reaction), and thus, information about the reaction mechanism. The length of time the single particle or single molecule resides in each state provides information about the kinetics of the reaction.

In another aspect, an apparatus for single particle or single molecule spectroscopy is provided which comprises an optical microcavity, the microcavity characterized by at least one resonance frequency; optical components configured to evanescently couple a probe laser beam into the microcavity; optical components configured to illuminate the surface of the microcavity with a free space pump laser beam such that the focal spot of the free space pump laser beam substantially overlaps with the single particle or single molecule; a detector configured to detect light from the probe laser beam; wherein the apparatus is configured to detect a change in an optical characteristic of the detected light due to a shift in the at least one resonance frequency induced by heat generated and transferred to the microcavity from a single particle or a single molecule in a sample in contact with the surface of the microcavity via energy absorbed by the single particle or single molecule from the free space pump laser beam. The apparatus may further comprise light sources configured to generate the probe laser beam and the free space pump laser beam. The source for the free space pump laser beam may be a wavelength-tunable source or the apparatus may comprise multiple light sources configured to generate pump laser beams at different wavelengths (e.g., in order to measure a pump-wavelength-dependent response, i.e., the absorption spectrum of the single molecule or particle). The apparatus may further comprise a sample cell configured to contain a liquid and the microcavity immersed in the liquid.

As discussed above with respect to the resonance tuning methods, a variety of optical and electrical components may be used in the apparatus. If a microscope objective is used to focus a pump laser beam onto the surface of the microcavity, it may be an objective having a sufficiently high numerical aperture in order to minimize the excitation volume.

In addition, the apparatus may further comprise a lock-in amplifier configured to pick out those frequency components of the transmitted light from the microcavity modulated at the same frequency as the amplitude modulation of the free space pump laser beam. (See FIG. 9, which is further described below.) The amplitude modulation of the free space pump laser beam may be in the range of from about 10 kHz to 1 MHz, or from about 1 kHz to 1 MHz, e.g., 4 kHz. At these frequencies, a single particle or single molecule may undergo multiple pump-induced photocycles, allowing a temperature change to build up. Fast modulation also has the benefits of allowing more repeat measurements to strengthen a weak signal, as well as moving away from 1/f noise present in electro-optical signals.

Figure 7:
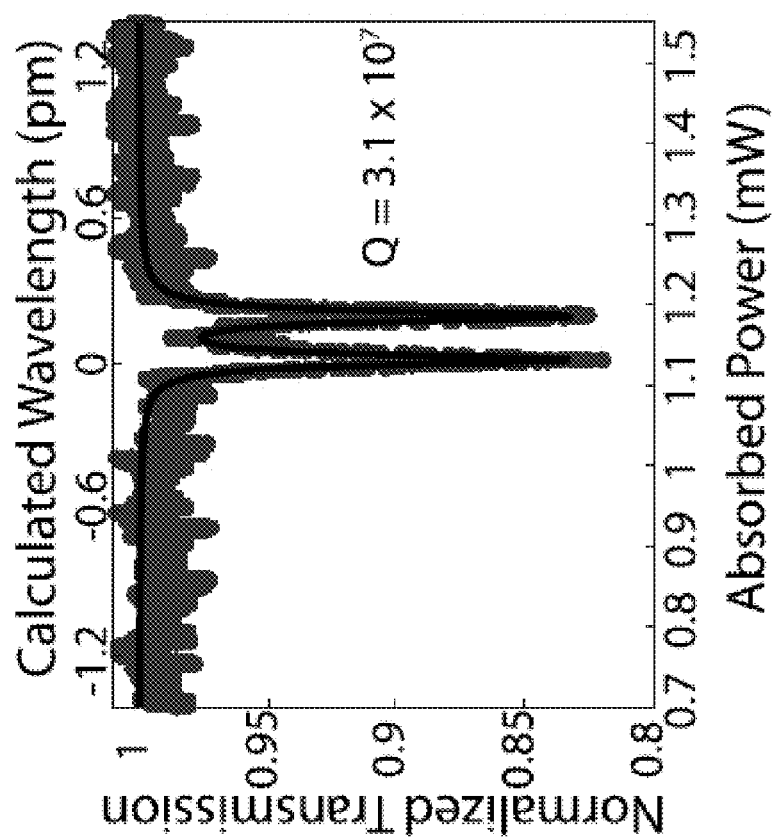
FIG. 7 shows a scan of toroid resonance shift versus photothermal heating, with Lorentzian fit. The probe wavelength was fixed at 1566.93 nm, while the pump laser power was scanned with a triangular waveform. The wavelength was calculated from the measured temperature dependence of the toroid resonance (3200 fm/mW).

The apparatus may further comprise a second detector configured to detect light from the probe laser beam back-scattered from the microcavity. (See FIG. 9, which is further described below.) Briefly, any defects on the surface of the microcavity serve to couple the propagating and counter-propagating modes, with the magnitude of the splitting proportional to the index change provided by the defect. (See Zhu, J. G.; Ozdemir, S. K.; Xiao, Y. F.; Li, L.; He, L. N.; Chen, D. R.; Yang, L.: On-chip single nanoparticle detection and sizing by mode splitting in an ultrahigh-Q microresonator. *Nature Photon.* 2010, 4, 122-122.) This splitting is seen in FIG. 7 (and further described in Example 1, below). The back-scattered signal intensity, resolvable using a fiber optic circulator, can be quantitatively related to the splitting, cleaning resolving extremely small time-dependent splitting even in the presence of significantly larger static splitting. (See Knittel, J.; Swaim, J. D.; McAuslan, D. L.; Brawley, G. A.; Bowen, W. P.: Back-scatter based whispering gallery mode sensing. *Sci. Rep.* 2013, 3, 2974.) Thus, the combination of Pound-Drever-Hall stabilization (as described above with respect to the resonance tuning methods and further, below) with the detection of back-scattered light can enable detection of resonance position fluctuations of 0.7 fm and a noise floor due only to photon shot noise and intensity fluctuations of the probe laser beam. (See Id.)

If a tapered optical fiber is used to evanescently couple the probe laser beam into the microcavity, the apparatus may comprise components for stabilizing the evanescent coupling of the tapered optical fiber. (See Knittel, J.; Swaim, J. D.; McAuslan, D. L.; Brawley, G. A.; Bowen, W. P.: Back-scatter based whispering gallery mode sensing. *Sci. Rep.* 2013, 3, 2974.)

The apparatus may comprise components for minimizing background absorption of the free space pump laser beam via spatial modulation as described in Arbouet, A., Christofilos, D., Del Fatti, N., Vallee, F., Huntzinger, J. R., Arnaud, L., Billaud, P., and Broyer, M.: Direct Measurement of the Single-Metal-Cluster Optical Absorption. *Phys. Rev. Lett.*, 2004, 93, 127401.

Figure 9:
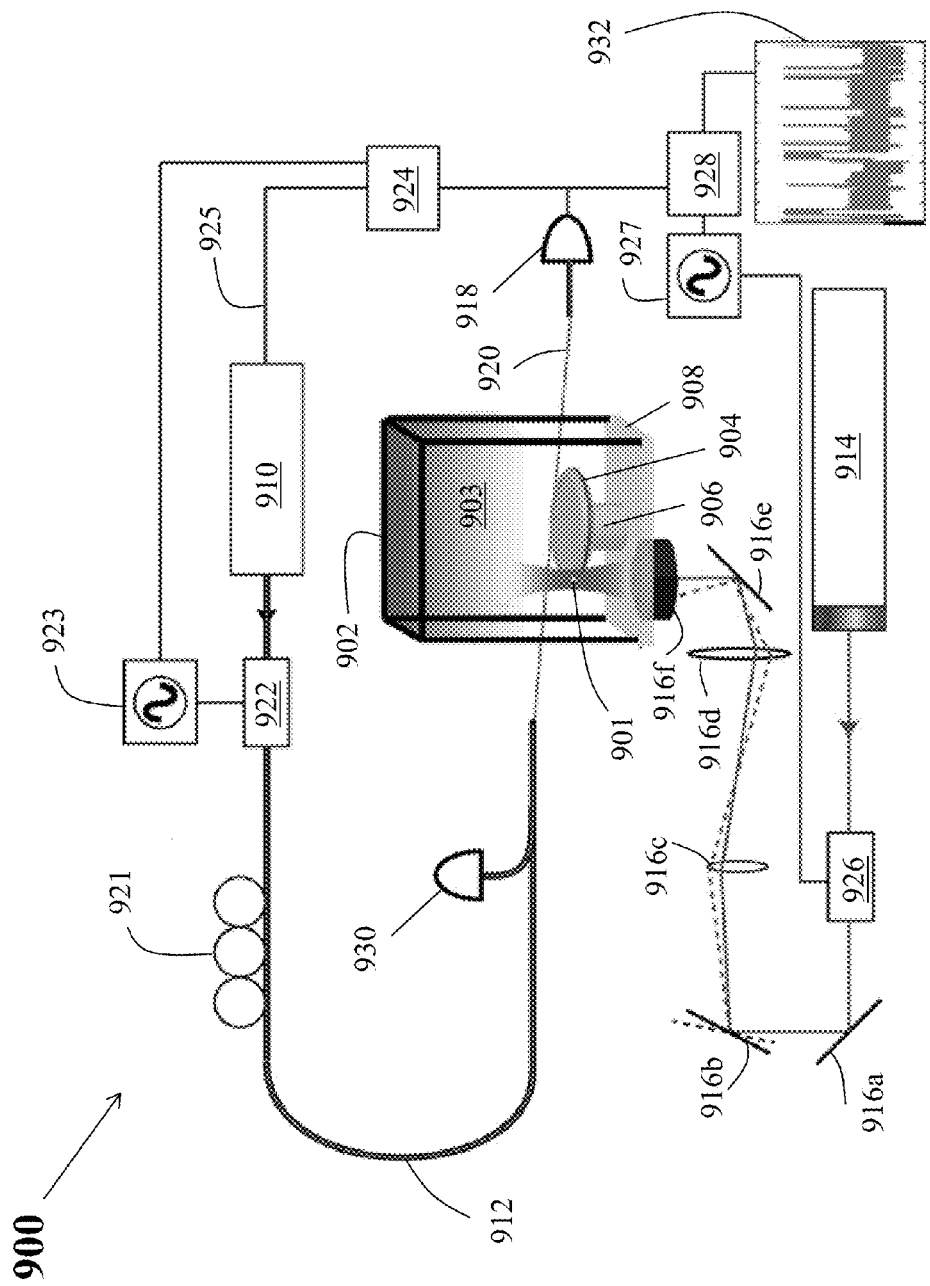
FIG. 9 shows an apparatus for carrying out single particle or single molecule spectroscopy according to an illustrative embodiment.

An embodiment of an apparatus 900 configured to perform single particle or single molecule spectroscopy on a single particle/molecule 901 is shown in FIG. 9. The apparatus 900 comprises a sample cell 902 configured to contain a liquid 903 (e.g., solvent or buffer solution) and a toroid microcavity 904 (i.e., microresonator) immersed in the liquid 903. The toroid microcavity 904 is supported by a pillar 906 and a base 908. The pillar 906 and base 908 may be composed of silica and may serve as the transparent host substrate upon which the toroid microcavity 904 was placed after removal from a silicon growth substrate.

The apparatus 900 further comprises a light source 910 (e.g., a tunable light source) configured to provide a probe laser beam and optical components, i.e., a tapered optical fiber 912, configured to receive the probe laser beam and to evanescently couple it into the toroid microcavity 904.

The apparatus 900 further comprises a light source 914 (e.g., a tunable light source) configured to provide a pump laser beam and optical components 916 *a-f* configured to receive the pump laser beam and to focus it onto the surface of the microcavity 904. These optical components include mirrors 916 *a, e*, a microscope objective 916 *f*, a servo-mounted gimbal mirror 916 *b* and relay optics 916 *c, d* configured to scan the pump laser beam across the surface of the toroid microcavity 904. These optical components do not deliver the pump laser beam to the surface of the microcavity 904 via the microcavity's propagating mode and thus, provide for illumination of the surface with a "free space pump laser beam." The focal spot of the free space pump laser beam substantially overlaps with the single particle/molecule 901. In this embodiment, the focal spot of the free space pump laser beam is also positioned substantially near the rim of the toroid microcavity 904 such that it substantially overlaps with the propagating mode in the toroid microcavity 904. The apparatus further comprises a detector 918 configured to detect fiber-coupled light 920 from the probe laser beam transmitted from the toroid microcavity 904. Signal from the detector 918 is shown in a plot 932 of transmitted power versus time.

The apparatus 900 further comprises optical components for manipulating the probe laser beam generated by the light source 910, including components 921 for polarization control and a phase modulator 922. The phase modulator 922 is part of a Pound-Drever-Hall (PDH) servo loop coupled to the probe laser beam for achieving stabilization of the probe laser beam via the PDH technique. The PDH servo loop comprises the phase modulator 922 which is driven by an oscillator 923 to generate a phase modulated probe laser beam comprising a carrier frequency and two side bands. The fiber-coupled light 920 detected by detector 918 is demodulated by components 924 to provide a signed error signal 925 which is fed back to the light source 910 to adjust the wavelength of the probe laser beam such that it remains substantially resonant with the microcavity 904.

The apparatus 900 further comprises optical components for manipulating the free space pump laser beam generated by the light source 914, including an amplitude modulator 926. The apparatus 900 further comprises a lock-in amplifier 928. The amplitude modulator 926 and the lock-in amplifier 928 are part of a lock-in amplification system coupled to the free space pump laser beam. The amplitude modulator 926 is driven by an oscillator 927 to generate an amplitude modulated free space pump laser beam. The lock-in amplifier 928 extracts components from the fiber-coupled light 920 detected by detector 918 which are modulated at substantially the same frequency as the amplitude modulated free space pump laser beam.

The apparatus 900 may include an additional servo loop to stabilize the distance between the toroid microcavity 904 and the tapered optical fiber 912. Such a loop may include additional modulators and demodulators.

As shown in FIG. 9, the apparatus 900 further comprises another detector 930 configured to detect light from the probe laser beam that is back-scattered from the toroid microcavity 904.

Due to the configuration of the pump laser beam and the free space pump laser beam as well as the selected wavelengths of these beams, in the disclosed spectroscopic methods and related apparatuses, single particles/molecules do not substantially absorb energy from the probe laser beam or the propagating mode in the microcavity. Rather, single particles/molecules absorb energy from the free space pump laser beam, thereby generating heat, and transferring the heat to the microcavity, thereby inducing a shift in at least one resonance frequency of the microcavity.

The disclosed methods and apparatuses will be understood more readily by reference to the following examples, which are provided by way of illustration and are not intended to be limiting.

EXAMPLES

Example 1

Resonance Tuning of Toroid Microcavities

This example demonstrates the tuning of the resonance of a toroid microcavity by modulating the position and intensity of a free-space visible, continuous wave (CW) pump laser whose output has been focused onto the resonator. By varying the power of the pump laser, a tuning ratio of $1.5 \times 10^5$ fm/mW was achieved on a silica toroid with a 2 μm diameter silicon pillar. A fraction of the heat generated from the silicon absorption is transferred to the silica, redshifting the resonant frequencies due to the positive thermo-optic coefficient of silica.

Toroidal microcavities are fabricated according to the procedure of D. K. Armani, T. J. Kippenberg, S. M. Spillane, and K. J. Vahala, Nature 421, 925 (2003) with a modification from J. B. Jager, V. Calvo, E. Delamadeleine, E. Hadji, P. Noe, T. Ricart, D. Bucci, and A. Morand, Appl. Phys. Lett. 99, 181123 (2011). Discs of thermally grown oxide 60 μm in diameter and 2 μm tall were patterned on silicon. A $SF_6$/Ar ICP etch was used to create a highly repeatable undercut in the silica disc. A $CO_2$ laser was used to selectively anneal the toroids (termed standard toroids). An additional etching step using $XeF_2$ vapor was optionally used to increase the undercut after the laser annealing step (termed re-etched toroids). (See M. Hossein-Zadeh and K. J. Vahala, Opt. Express 15, 166 (2007).) Q-factor>$10^7$ was measured on multiple re-etched toroids, indicating that the re-etching step did not compromise the ultrahigh Q-factor. A standard toroid 100 is shown in FIG. 1 and a re-etched toroid 200 is shown in FIG. 2.

An external cavity diode laser (New Focus, 1560 nm) was coupled into toroids via tapered optical fiber. (See D. K. Armani, T. J. Kippenberg, S. M. Spillane, and K. J. Vahala, Nature 421, 925 (2003).) Typical coupled powers ranged from 40-150 nW to avoid nonlinear thermal effects. A fixed-wavelength-CW diode laser (Blue Sky Research, 640 nm) was focused to a 2 μm diameter spot with a 40×0.75 NA microscope objective. A gimbal-mounted mirror positioned at an optical plane conjugate to the back aperture of the objective was used to control the position of the laser spot in the toroid plane.

Figure 3B:
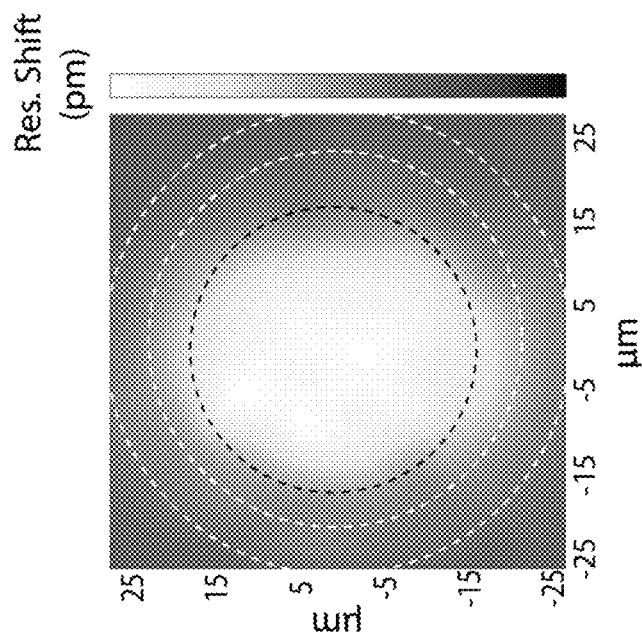
FIGS. 3A-B show the photothermal map of the spatial dependence of resonance shift for the structure of FIG. 1. The map is constructed from 13×13 grid with 4 μm increment, where each shift at constant (4.2 mW absorbed) pump power is referenced to the shift with no external pump. In (B), white dotted lines representing the outline of the toroid and black dotted lines representing the outline of the pillar are superimposed on the map, showing the correlation between maximum shift and the silicon pillar.
Figure 3A:
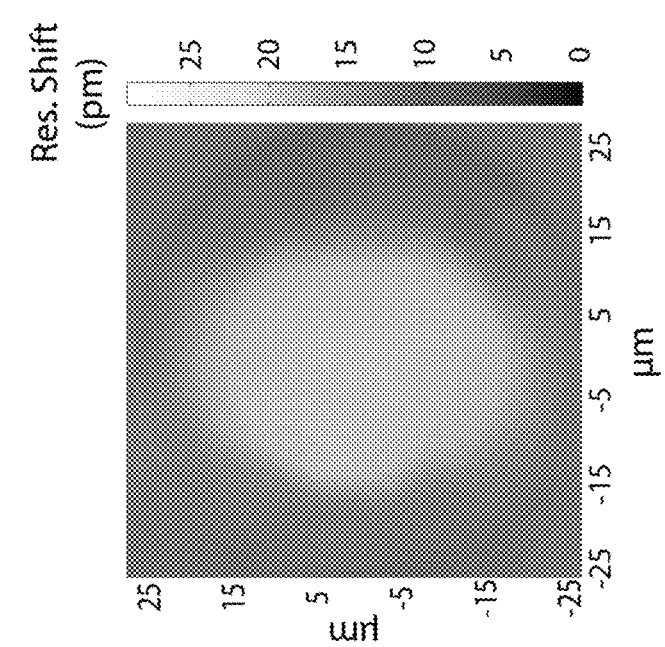
Figure 4B:
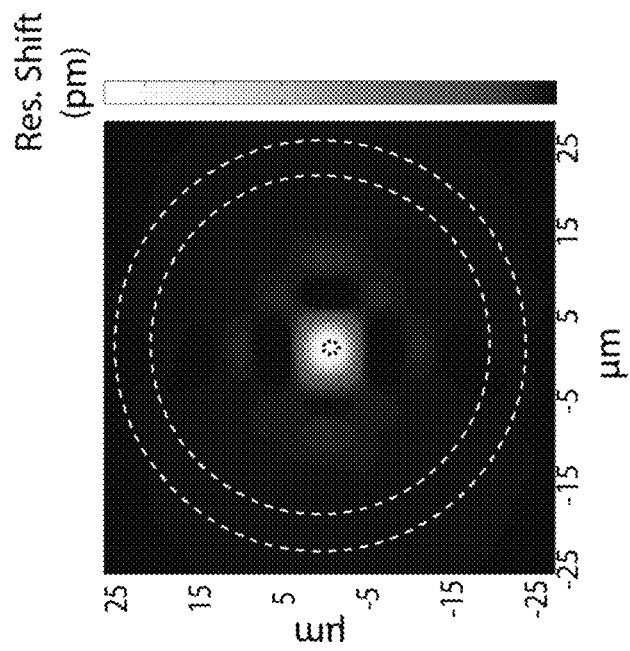
FIGS. 4A-B show the photothermal map of the spatial dependence of resonance shift for the structure of FIG. 2. The map is constructed from 13×13 grid with 4 μm increment, where each shift at constant (4.2 mW absorbed) pump power is referenced to the shift with no external pump. In (B), white dotted lines representing the outline of the toroid and black dotted lines representing the outline of the pillar are superimposed on the map, showing the correlation between maximum shift and the silicon pillar.
Figure 4A:
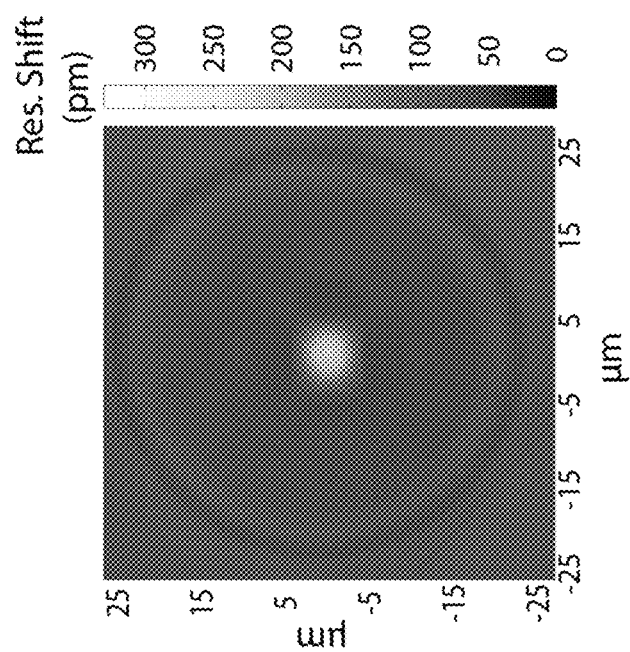
Figure 5:
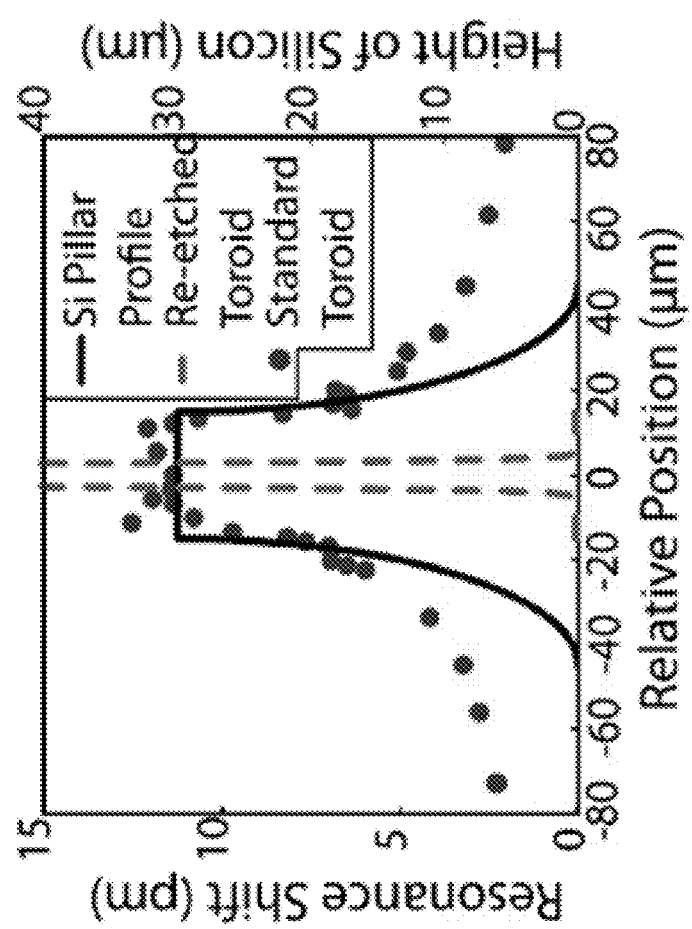
FIG. 5 shows photothermal linescans of a standard and re-etched toroid. The laser spot was scanned laterally across the center of the toroid at constant power (4.2 mW absorbed) and the resonance shift measured as a function of laser position. The profile of the silicon pillar is shown for the standard toroid (black), the resonance shift is shown for the standard toroid (circles), and the resonance shift is shown for the re-etched toroid (dashed line). The re-etched toroid is significantly more sensitive.
Figure 6:
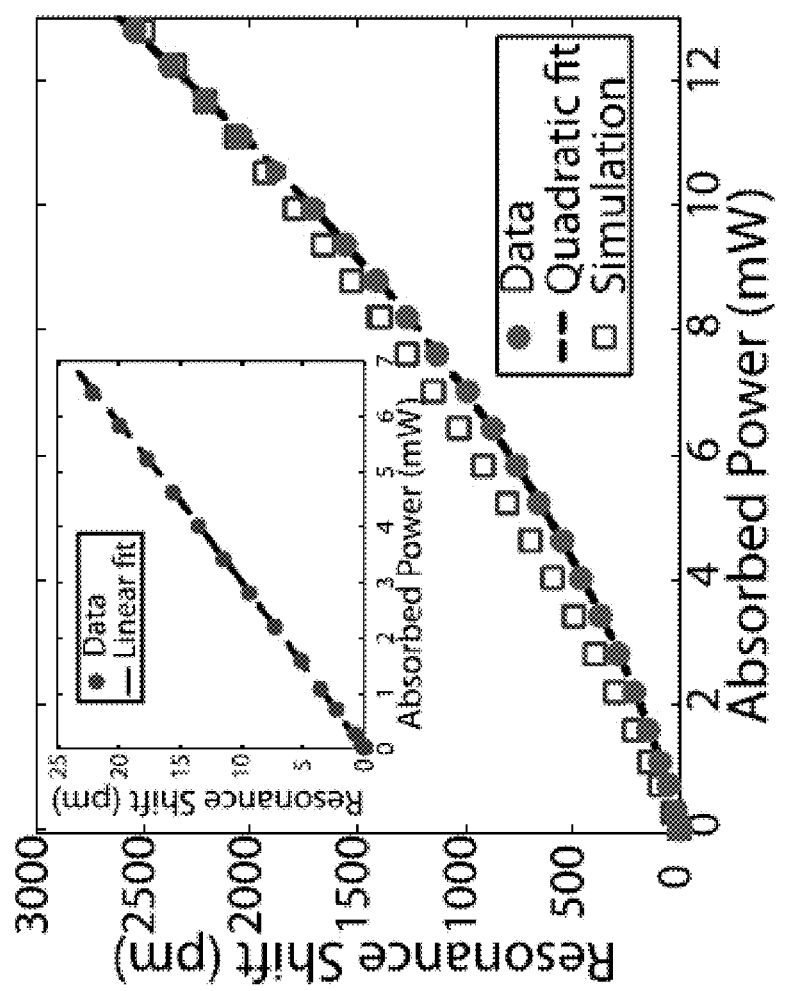
FIG. 6 shows the power dependence of photothermal shift. The shift is seen to be quadratic for a re-etched toroid and to extend to over half the free spectral range (FSR) of the resonator. Simulations capture the quadratic power dependence and were performed by calculating equilibrium temperature at the silica rim from the measured pump power and extrapolating resonance shift with Equation 1 (see Example 1, below). Error bars are present but too small to see on this scale. The inset shows the results for a standard toroid, showing a shallower slope and linearity over the range examined.

Resonance shift of the toroid was spatially mapped by scanning the pump beam over the resonator and surrounding area as shown in FIGS. 3 and 4. FIG. 3 is a photothermal map of the structure shown in FIG. 1 and FIG. 4 is a photothermal map of the structure shown in FIG. 2. The laser spot was small compared to the size of the resonator, enabling a high-resolution map. The maximum shift was closely associated with illuminating the silicon pillar where the shift was essentially constant with position. Resonance shift as a function of the position of the pump beam relative to the center of the toroids is shown in FIG. 5 for the re-etched toroid (dashed line) and the standard toroid (circles). Resonance shift as a function of power of the pump beam is shown in FIG. 6 for the re-etched toroid and the standard toroid (inset). The resonance shift, 3200 fm/mW pump power, was approximately five times larger on the silicon pillar than when the spot position was well-separated (80 μm) from the toroid. Decreasing the size (diameter) of the toroid support pillar with an additional etching step (re-etched toroid) significantly amplifies the effect and the slope rises to $1.5 \times 10^5$ fm/mW, without compromising the Q-factor. The high power density ($10^8$-$10^9$ W/cm$^3$) in the heated volume drives the high sensitivity of this tuning method. The increased sensitivity of the re-etched toroid is attributed to the reduced heat capacity of the smaller silicon pillar, leading to a greater temperature increase at the silicon-silica interface, and consequently greater equilibrium temperature at the mode-carrying silica.

To understand the relevant heat flows, numerical simulations were performed in COMSOL Multiphysics (the simulations are described in more detail below). The redshift in resonance wavelength (Δλ) as a function of the change in temperature is given by $$\lambda_T - \lambda_0 = \Delta\lambda = \frac{\lambda_0}{n_0} \times \frac{dn}{dT}(T) \times (T - T_0) \qquad \text{Equation 1}$$

where $\lambda_0 = 1.566$ μm, $n_0 = 1.444$ and $$\frac{dn}{dT}(T) = 2.6 \times 10^{-8} K^{-2} \times T + 7.5 \times 10^{-7} K^{-1},$$

an expression derived from linear extrapolation of data from V. S. Il'chenko and M. L. Gorodetskii, Laser Phys 2, 1004 (1992). As shown in FIG. 6 (squares), the model accurately matches the experimental power dependence. As shown in the inset of FIG. 6, over a tuning range of 0-25 pm for a standard toroid, the tuning curve is linear, with a slope of 9.2 pm/K. At the much greater shifts possible with a re-etched toroid, the shift appears quadratic in both simulations and experiments due to the temperature dependence of the thermo-optic coefficient $$\left(\frac{dn}{dT}\right).$$

At 12.7 mW of pump laser power, the silica heats up to 443 K. At larger pump powers (>2 mW absorbed), the re-etched toroid resonances exhibited minor spectral fluctuations consistent with intensity noise in the pump laser.

The strengths of this approach are versatility of control and sensitivity. As shown in FIG. 6, continuous and convenient tuning of resonance position over more than one half of the resonator's free spectral range (FSR) has been demonstrated, limited by the power of the pump laser. Alternatively, as little as 1 μW shifts the resonance by one full width at half maximum (FWHM), a low-power switch. As a demonstration of the elimination of the need for a tunable probe, FIG. 7 shows that ultrahigh-Q factors are observed by photothermally tuning the resonance and probing at a fixed wavelength. The splitting of the resonance is caused by backscatter-induced degeneracy lifting of the clockwise and counterclockwise whispering gallery mode (WGM) and is routinely observed in toroidal microcavities. Control over multiple orders of magnitude of spectral position is a highly useful experimental parameter.

Figure 8:
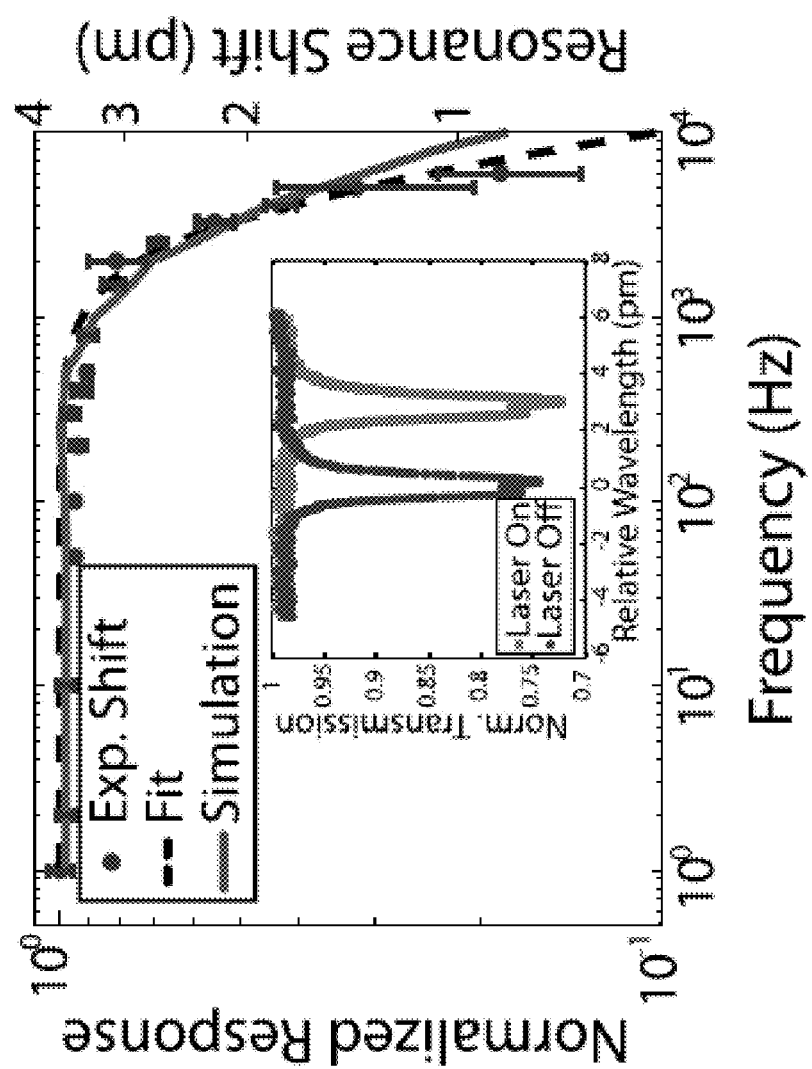
FIG. 8 shows the frequency response of a standard toroid during pump beam modulation (circles). The toroid has a cutoff frequency of 4200 Hz, and was fit with exponential time dependence (dashed line, $1-e^{(-t/\tau)}$). Simulation (solid line) predicts a cutoff frequency of 5000 Hz. The inset shows a scan of resonance with pump laser off (black) and on (grey).

The timescale of the resonance shift, a critical parameter for optical switching applications, was measured by modulating the pump beam with a square wave while recording the relative position of the modulated and un-modulated resonance. The maximum wavelength shift was set (by controlling the pump intensity) to 2.8 pm, ~30 linewidths for $Q=1.5*10^7$. A shift of only several linewidths is sufficient for switching. When the time interval falls below the thermal equilibration time of the toroid the shift decreases. FIG. 8 shows a modified Bode magnitude plot of a standard toroid demonstrating a cutoff frequency of 4200 Hz, over an order of magnitude faster than previously reported thermal control mechanisms. (See D. Armani, B. Min, A. Martin, and K. J. Vahala, Appl. Phys. Lett. 85, 5439 (2004).) Time-dependent simulations predict a comparable cutoff of 5000 Hz on a standard toroid. The re-etched toroid has a lower cutoff frequency of 400 Hz, likely due to the larger path length for heat to travel through the silica between the silicon pillar and the silica rim.

In summary, a highly versatile method of tuning the resonance position of toroidal microcavities was demonstrated. A visible, fixed-wavelength laser at modest power was used to reproducibly shift the resonance by a few to more than 10,000 times the FWHM. This technique places few requirements on the wavelength, linewidth, or tunability of the pump beam. Re-etching the silicon pillar greatly increases the sensitivity without compromising the ultrahigh-Q. The re-etched toroid can be continuously tuned over half the FSR, with fast modulation times. These toroids can also be switched over one FWHM with approximately 1 μW of pump beam power, an important consideration for optical processing. This method reduces the need for expensive tunable probe sources, as now a simple and inexpensive pump laser can be used to shift the resonance of a microcavity to be resonant with a fixed wavelength probe.

Simulations: Photothermal effects on the toroid were modeled with the Heat Transfer Module of COMSOL Multiphysics. The physical dimensions of the toroid were extracted from side-view SEM images (see FIGS. 1 and 2). Air around the toroid and a silicon substrate were included. Heating by the pump laser was modeled by a series of five 1-μm thick cylindrical heat sources of decreasing intensity. The total heat generated was equal to the incident optical power adjusted by the measured reflectivity of 2 μm of thermal oxide on silicon at 640 nm (R=0.24). The heat was divided among the five heating regions with a decaying exponential corresponding to the penetration depth of 640 nm light in silicon. The volume of silicon heated by the laser was approximately 10 μm$^3$, given by the product of the spot size and penetration depth in silicon at 640 nm (3.3 μm). Equilibrium temperature was calculated by solving for the stationary solution to conductive heat transfer. Convection was found to negligibly affect the observed temperature increase (<1%), and was not included in the simulations. Material properties, except for the thermo-optic coefficient (discussed below) were taken from the COMSOL library. Small changes in the size distribution of the heat sources were found to contribute only minor variations to calculated thermal properties. Resonance shifts were calculated from the equilibrium temperature of the silica rim, which was found to be highly uniform with the pump beam centered on the toroid. The thermal expansion of silica is an order of magnitude smaller than the thermo-optic effect and was neglected in these calculations. (See J. W. Berthold, S. F. Jacobs, and M. A. Norton, Metrologia 13, 9 (1977).) In the low-power regime the thermo-optic coefficient of the silica can be assumed to be constant, with a value of $8.5*10^{-6}$/K. (See Douglas B. Leviton and Bradley J. Frey, Proc. SPIE-Int. Soc. Opt. Eng. 6273, 62732K (2006).) At greater shifts the temperature dependence of the thermo-optic coefficient had to be accounted for (see FIG. 6 and above). Time-dependent simulations were conducted with all the parameters identical to the stationary simulations.

Reproducibility and Stability: Subtle differences in fabrication conditions, including the $CO_2$-reflow process, resulted in differences between the tuning curves of individual toroids. Data showed the variation in spatial linescans between four unique standard toroids. The peak resonance shift at constant power (4.1 mW absorbed) yielded the slope-to-slope variation in photothermal tuning between toroids. The slope varied by as much as 35% between toroids. However, the shape of the linescan did not vary between different toroids. Importantly, slope-to-slope variations of the tuning curve do not constitute a disadvantage of the approach presented in this example, as individual toroids can still be conveniently controlled.

Measuring the Q-factor of toroidal resonances by photothermally tuning the resonance wavelength and probing at a fixed wavelength was comparable to the traditional method of scanning the wavelength of the probe laser with no pump beam. As described above, FIG. 7 was obtained via photothermal tuning. The same resonance on the same toroid was measured on a different day, via wavelength scanning. The measured Q-factor ($1.5 \times 10^7$) was not significantly different.

Using the pump beam to offset the resonance wavelength did not significantly change the Q-factor. A transmission spectrum of a re-etched toroid was obtained under pump beam illumination (4.1 mW absorbed, the same power used in the photothermal maps of FIGS. 3 and 4). Although the center wavelength of the resonance shifted by 460 pm relative to the unperturbed resonance, the Q-factor remained essentially the same ($2.2 \times 10^7$) as compared to the measurement at zero photothermal shift ($1.5 \times 10^7$) or the measurement by photothermally tuning the resonance at low power ($3.1 \times 10^7$, FIG. 7). In this case, a singlet was seen, consistent with the stochasticity of resonance splitting.

Stability of the resonance wavelength under weak or moderately intense pump beam illumination did not greatly differ from that with no pump beam. Scan-to-scan shifts in the center wavelength of the resonance measured at zero photothermal shift yielded a standard deviation in peak center position of 33 fm with no pump power (resonance FWHM was 51 fm) and increased to 70 fm at 1.2 mW absorbed pump power, a modest increase given the large offset (~2,500 linewidths).

As mentioned above, fluctuations in the resonance position were observed when pumping re-etched toroids with higher pump beam power. A representative transmission scan of the toroid resonance at 4.1 mW absorbed power was obtained in which the wavelength of the probe laser was scanned over a 5.3 pm range in 50 ms. The resonance position changed, and crossed the scanning wavelength of the probe laser several times during the scan, although ultrahigh Q-factor was maintained ($Q > 1 \times 10^8$). This scan suggests that the resonance shifts on a timescale faster than the scan speed (5.3 pm in 50 ms), but remains essentially constant in the time it takes to cross over a single resonance (~190 µs to cover ~20 fm). Such fluctuations were not observed on standard toroids, and were not observed at low power on the re-etched toroid. Characterization of the pump laser intensity revealed the presence of moderate (up to several %) and intermittent intensity fluctuations that varied over multiple time scales from µs to ms. At the 4.1 mW pump in the transmission scan, variations in pump power of 1% would result in peak shifts of several pm, consistent with what was observed. These fluctuations were also found to vary with the tension on the fiber optic taper, increasing when the taper loosened and decreasing when it was tightened. When tensioned, the shifts were partially but not completely mitigated. It is likely that the fast and intermittent variations in pump intensity of the pump diode laser were the dominant contributor to these fluctuations.

Frequency Response: The frequency response of re-etched toroids to pump beam modulation was investigated. A much lower cutoff frequency was observed (400 Hz vs. 4200 Hz in a standard toroid). This is attributed to the much smaller interfacial region between the silicon pillar and the bulk silicon of the underlying substrate, which constricts the rate of heat transfer between the toroid and the underlying substrate. This is consistent with the much higher temperatures achieved at the same pump power on re-etched toroids.

Example 2

Electronic Absorption Spectrum of a Single Molecule

Single molecules of cobalt phthalocyanine (CoPc) will be studied with the disclosed spectroscopic methods using an apparatus similar to that shown in FIG. 9. CoPc possesses an excited state lifetime ($\tau$) of ~2 ps and an extinction coefficient ($\epsilon$) of 34,000 L mol$^{-1}$ cm$^{-1}$. The rate of electronic transition upon CW excitation was calculated using the following relation, $$\text{Transitions/s} = \frac{\sigma I}{h\nu}$$

where I is the pump intensity in W/cm$^2$, $\sigma$ is the absorption cross section in cm$^2$, and $\nu$ is the excitation frequency, yielding $3.5 \times 10^{10}$ transitions per second with a pump beam intensity of $7.8 \times 10^7$ W/cm$^2$. The transition rate translates into a thermal dissipation rate of 10 nW per molecule. The saturation intensity, $I_s$, of CoPc was calculated as $$I_s = \frac{h\nu}{2\sigma\tau}$$

which leads to a value of $5.6 \times 10^8$ W/cm$^2$, nearly an order of magnitude above the power of the pump of $7.8 \times 10^7$ W/cm$^2$. (See Moerner, W. E.; Fromm, D. P.: Methods of single-molecule fluorescence spectroscopy and microscopy. *Rev. Sci. Instrum.* 2003, 74, 3597-3619.) Notably, pumping at intensities close to or above $I_s$ will yield only marginal increases in dissipated thermal energy but larger increases in background.

The temperature rise in the microresonator as a result of a 10 nW heat source was determined by performing a finite element simulation in the package COMSOL Multiphysics. Assuming a silica microring on a silicon support pillar surrounded by air, the calculated temperature distribution was obtained. In the immediate vicinity of the molecule, the temperature rise was nearly 20 mK. To calculate the observed resonance shift, the index of refraction shift as a result of the increased temperature using silica's thermo-optic coefficient, dn/dT was calculated. Next, the electric field intensity distribution of the propagating optical mode was calculated. (See Oxborrow, M.: Traceable 2-D finite-element simulation of the whispering-gallery modes of axisymmetric electromagnetic resonators. *IEEE Trans. Microw. Theory Tech.* 2007, 55, 1209-1218.) Taking the three-dimensional overlap integral between the normalized electric field distribution and the spatially mapped refractive index change yields a new effective refractive index, $n_{eff}$, experienced by the propagating mode. This $n_{eff}$ was converted to a resonance shift via the relation, $$\Delta\lambda = \frac{2\pi r(n - n_{eff})}{m}$$

where r is the toroid major radius, n is the room temperature refractive index, and m is the mode number. Thus, a 10 nW source was calculated to provide a resonance shift of 7 fm, nearly 20 times higher than the smallest measured resonance shifts of 0.4 fm and a value that is convenient to measure, even without implementation of sophisticated noise eliminating instrumentation. (See Knittel, J.; Swaim, J. D.; McAuslan, D. L.; Brawley, G. A.; Bowen, W. P.: Backscatter based whispering gallery mode sensing. *Sci. Rep.* 2013, 3, 2974 and He, L. N.; Ozdemir, K.; Zhu, J. G.; Kim, W.; Yang, L.: Detecting single viruses and nanoparticles using whispering gallery microlasers. *Nature Nanotech.* 2011, 6, 428-432.) The 7 fm shift translates into a shift of one half of the peak's FWHM of 15 fm with $Q=1\times10^8$. This value is also in rough agreement with the experimentally observed photothermal shifts from pumping the silicon post in Example 1: the tuning curve in FIG. 6 is linear at low absorbed power and gives a slope of 0.07 fm/nW, translating into a resonance shift of 0.7 fm with 10 nW absorbed power. This is a lower limit, since when pumping the pillar, a substantially higher fraction of the thermal energy will be partitioned into the chip and away from the propagating mode. Thus, the heat dissipated from a single CoPc molecule will be shown to produce a distinct, measurable shift in the resonance peak.

After elimination of silicon from the apparatus (as described above), the main source of background signal will be the absorption of pump light by the silica. To generate the $7.8\times10^7$ W/cm² pump beam, a high NA objective will be used to focus the light through the transparent glass substrate to a near diffraction-limited spot of radius, 300 nm. Focusing 55 mW to this small area will yield the desired pump intensity. At 648 nm, silica attenuates light at a rate of 3 dB/km, a value consistent with the ability to maintain ultrahigh Q's at near this wavelength. (See Pinnow, D. A.; Rich, T. C.; Ostermay, F. W.; Didomeni, M.: Fundamental Optical Attenuation Limits in Liquid and Glassy State with Application to Fiber Optical Waveguide Materials. *Appl. Phys. Lett.* 1973, 22, 527-529 and Armani, A. M.; Kulkarni, R. P.; Fraser, S. E.; Flagan, R. C.; Vahala, K. J.: Label-free, single-molecule detection with optical microcavities. *Science* 2007, 317, 783-787.) Passage of 55 mW through 2 μm of silica at the edge of the toroid radius will result in 0.08 nW being absorbed. Assuming all of this energy is dissipated as heat, this translates into <1% of the expected single molecule signal.

Time-dependent finite element simulation of a 10 nW source on a microresonator indicates that equilibration to the full 7 fm shift takes approximately 1 ms. This timescale is consistent with the characterization of the microresonator's cut-off frequency with a square-wave modulated pump beam of 4.2 kHz as shown in Example 1. However, substantial fractions of the effect are reached after only a few 10's of μs. Thus, as described above, fast modulation of the pump beam will be used to enhance single molecule signal. Assuming a Lorentzian lineshape for the toroid resonance and a probe beam at constant wavelength, calculations have shown that modulation at 100 kHz yields a shift in the transmitted intensity with a signal-to-background of $1:10^2$.

Calculations of the resonance shift from a 10 nW source on a toroid immersed in water (as opposed to air) have shown a resonance shift of 1 fm, a smaller value due to water's greater heat capacity and thermal conductivity than air. However, this shift is well above the smallest shifts that have been measured (0.4 fm). In addition, the higher dielectric constant of water causes the propagating mode in the microcavity to protrude closer to the outer edge of the resonator, leading to better overlap with the region of temperature increase surrounding the single particle or single molecule, thus partially offsetting the reduction. (See Choi, H. S.; Zhang, X. M.; Armani, A. M.: Hybrid silica-polymer ultra-high-Q microresonators. *Opt. Lett.* 2010, 35, 459-461.)

Example 3

Imaging of Single Nanofibers

Figure 10:
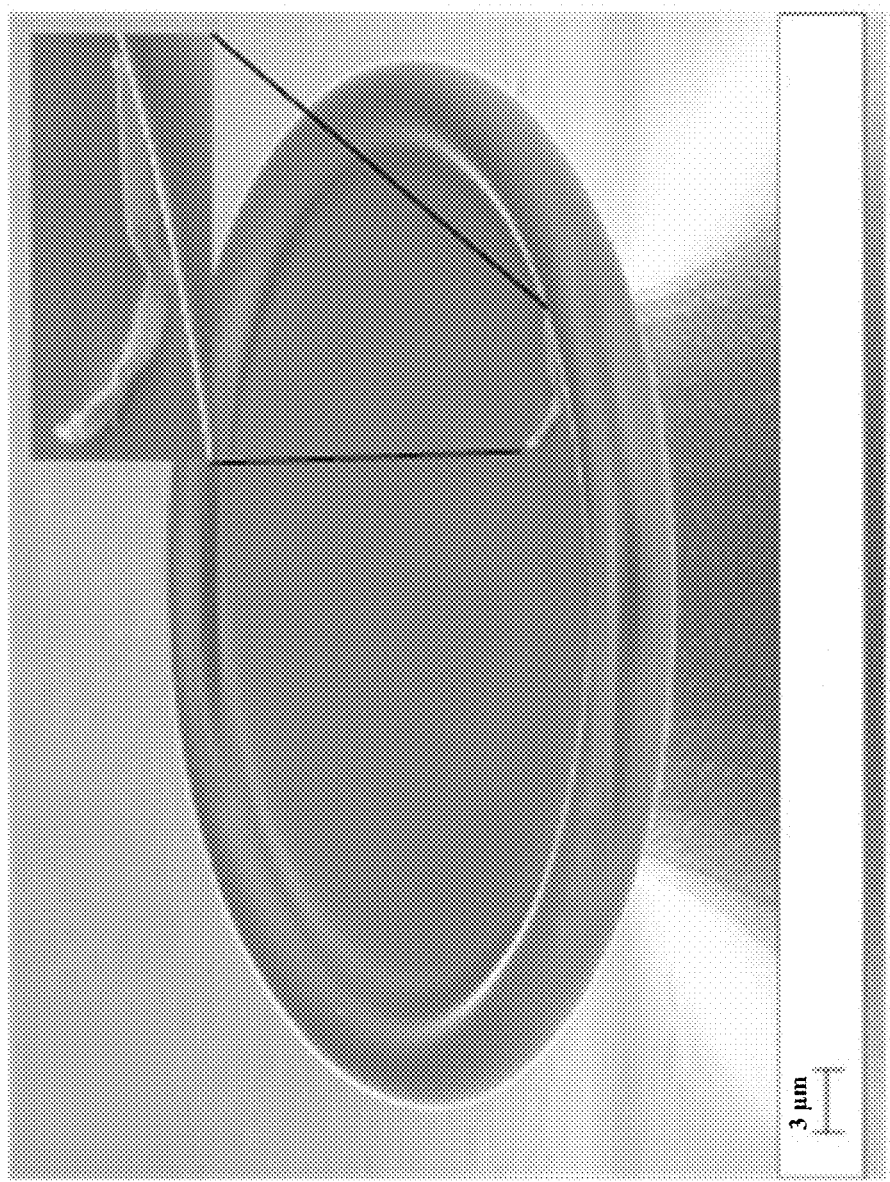
FIG. 10 shows a SEM image of a toroid microcavity with a single carbon nanofiber deposited on the surface of the microcavity.
Figure 11:
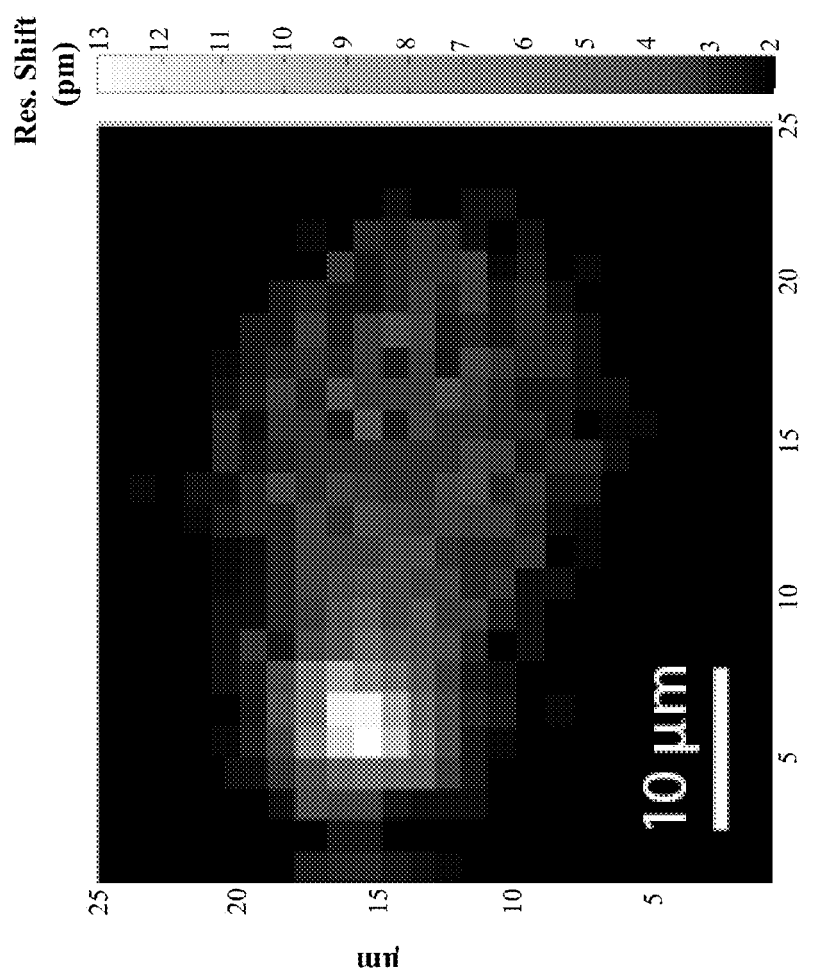
FIG. 11 shows the photothermal map of the spatial dependence of resonance shift for a portion of a toroid microcavity with a single carbon nanofiber deposited on the surface of the microcavity.
Figure 12:
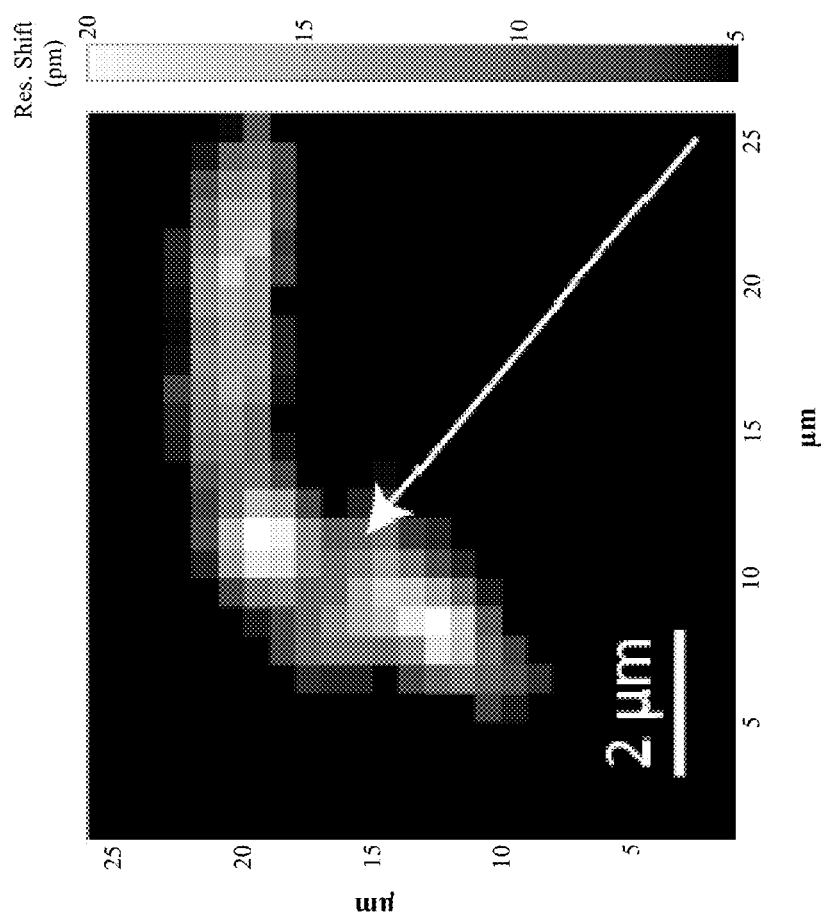
FIG. 12 shows a high resolution photothermal map of the spatial dependence of resonance shift for a portion of a toroid microcavity with a single carbon nanofiber deposited on the surface of the microcavity.

The experimental setup of Example 1 was used to image single carbon nanofibers on toroid microcavities. As shown in FIG. 10, single carbon nanofibers were deposited onto the surface of microcavities. Resonance shifts of the toroids were spatially mapped by scanning the pump beam over the microcavities. Two photothermal maps for two different microcavities are shown in FIGS. 11 and 12. The maps show that illumination of the carbon nanofibers by the pump beam results in a detectable resonance shift, due to the absorption of pump beam energy by the carbon nanofibers, the generation of heat and the transfer of heat to the microcavity to induce a shift in the resonance frequencies of the microcavity. The maps also resolve the structural conformation of some of the carbon nanofibers. For example, as shown in FIG. 12, a structural kink in a carbon nanofiber correlates to a decrease in resonance shift (arrow), due to the increased distance between the carbon nanofiber and the surface of the microcavity at the kink. Using the spectroscopic methods described above with a wavelength-tunable free space pump laser beam, spectroscopic studies of the single carbon nanofibers may be performed.

Example 4

Photothermal Microscopy of Non-luminescent Single Particles Enabled by Optical Microresonators This example demonstrates a powerful new paradigm for single-particle microscopy on non-luminescent targets using ultra-high Quality factor optical microresonators as the critical detecting element. The approach is photothermal in nature, as the microresonators were used to detect heat dissipated from individual photoexcited nano-objects, thereby allowing not simply detection of the nanoobjects, but also their spectral measurement. The approach couples the sensitivity of label-free detection using optical microresonators with a means of deriving chemical information on the target species, a significant benefit. In this example, individual non-photoluminescent multi-walled carbon nanotubes were spatially mapped and the per-atom absorption cross-section was determined. The individual multi-walled carbon nanotubes (MWCNTs) were pumped with a focused free-space laser. The local increase in temperature caused by heat dissipation from the absorbing nanotube redshifted the resonant wavelength of the microresonator due to the positive thermo-optic coefficient of silica. A resonance shift of almost 40 linewidths was observed at modest pump power ($Q=3.3\times10^6$, $I_{pump}=9\times10^4$ W/cm²). Photothermal shifts as a function of excitation beam position and input polarization were used to image the nanotubes and explore their electronic transitions. Finite-element simulations were employed to model the relevant thermal processes and elucidate the sensing mechanism. Finally, the extension of this new technique to single molecules is provided.

Figure 13:
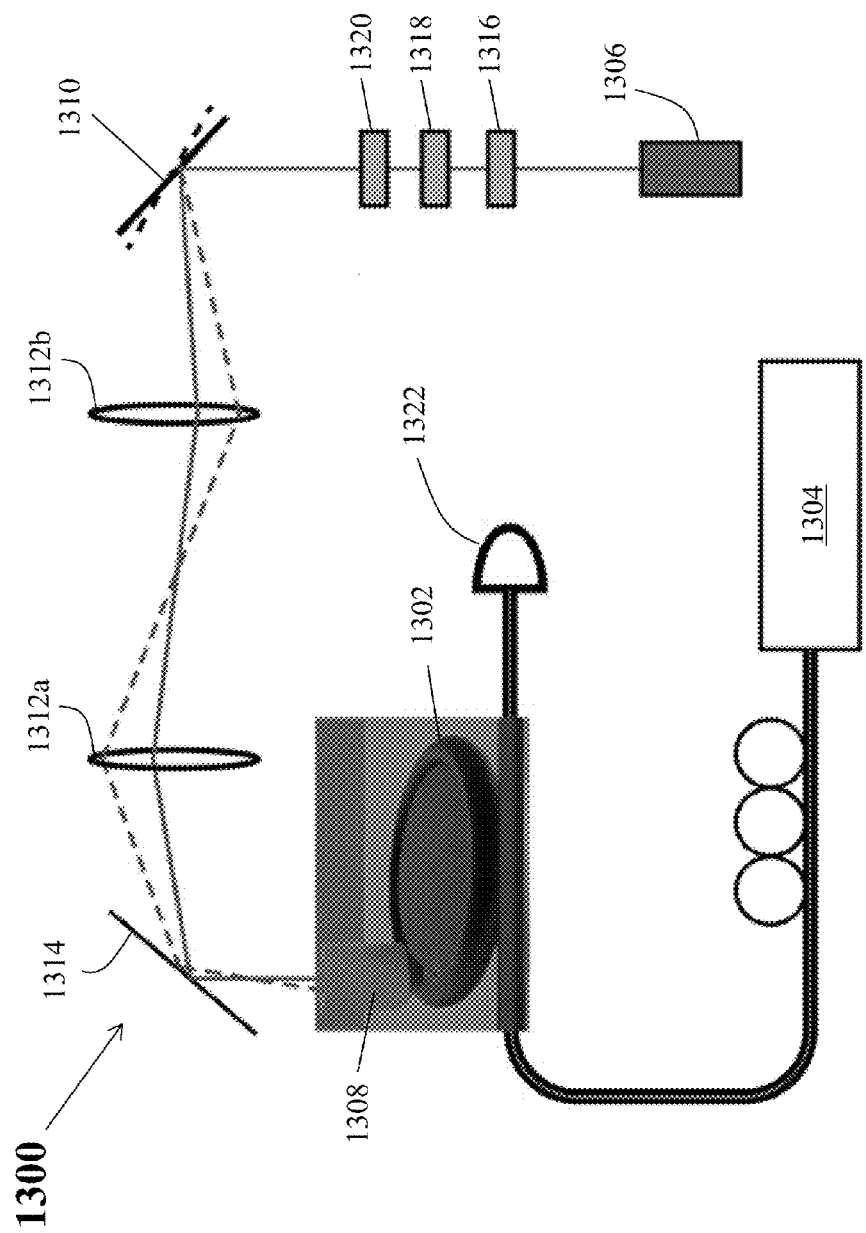
FIG. 13 depicts a schematic of an apparatus for single particle spectroscopy according to an illustrative embodiment.

Toroidal microresonators, similar to those shown in FIGS. 1 and 10, were fabricated by lithographically defining silica discs on a silicon substrate and undercutting the silica with an isotropic $SF_6$/Ar etch. This procedure was followed by a laser-induced reflow step. The details of the fabrication process have been provided in Example 1. Toroidal optical microresonators were used due to their unique combination of ultra-narrow linewidths and small mode volumes. The experimental set-up 1300 is illustrated in FIG. 13. Probe light was coupled into the microresonator 1302 via a tapered optical fiber controlled by a 3-axis piezopositioner (Attocube ECS 3030). Two orthogonal microscopes were used for alignment (Navitar Ultrazoom) and excitation beam delivery (Nikon FN1). A fiber-coupled tunable diode laser 1304 (New Focus, Velocity, 1560 nm) was used to probe the resonant wavelengths. The fiber-coupled probe power was kept low (~250 nW) to avoid thermal broadening of the toroid resonance. Nanotubes were photoexcited with a pump beam 1306 (Blue Sky Research, 640 nm) focused by a microscope objective 1308 (60×, 0.95 NA, Nikon) to a near-diffraction-limited spot (780 nm $1/e^2$ diameter). A gimbal-mounted mirror 1310 placed at a plane conjugate to the objective 1308 back aperture was used to control the beam position on the resonator 1302. The system also included relay optics 1312 $a,b$ and another mirror 1314. A polarizer 1316 and half-wave plate 1318 were used to adjust the linear polarization angle at the target nano-object. The system also included filter 1320 and detector 1322.

Figure 14:
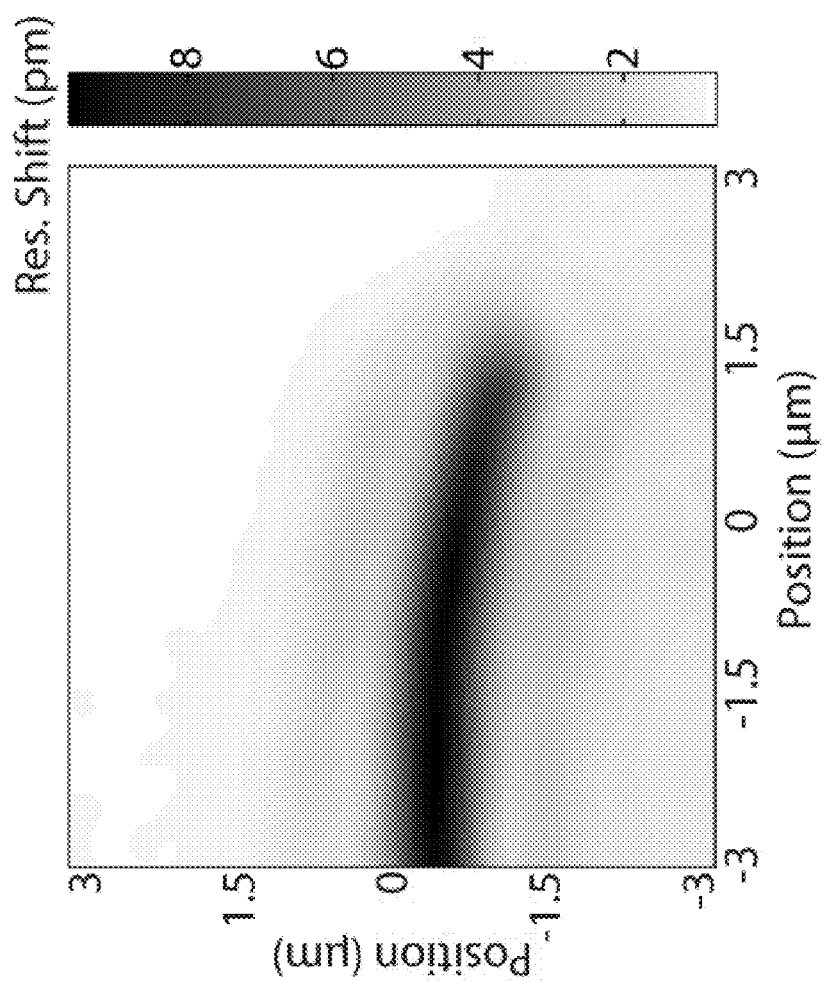
FIG. 14 shows a representative sample of a photothermal map taken on an individual nanotube. Incident power was 440 μW, resolution=250 nm/pixel, each pixel was an average of five scans.
Figure 15A:
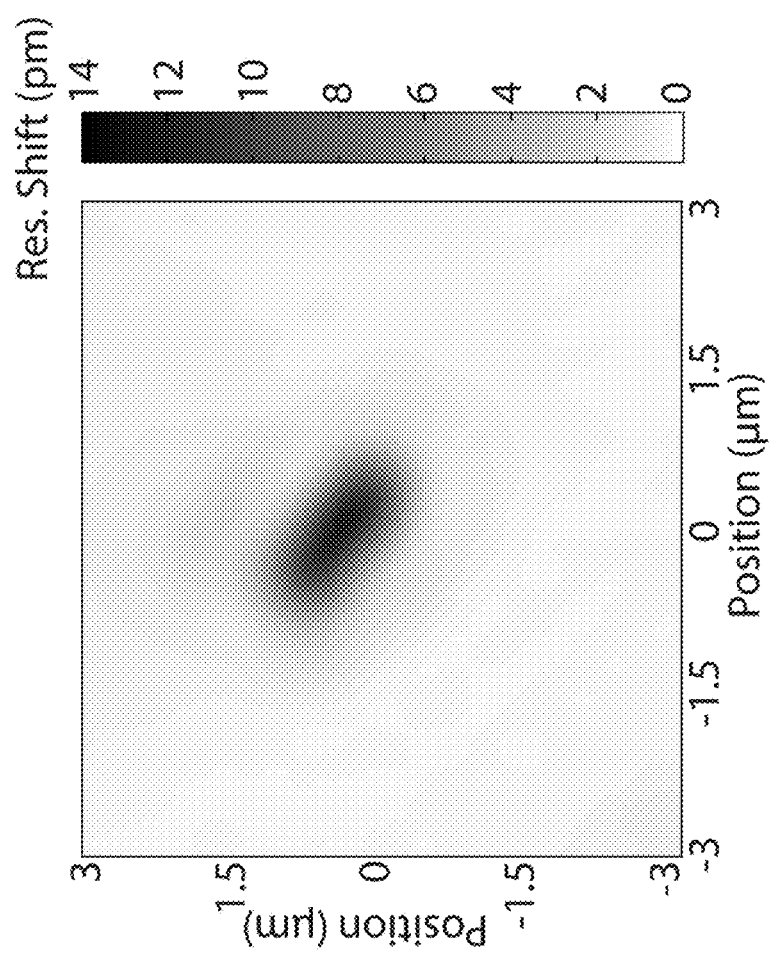
FIG. 15A shows the photothermal map of the MWCNT. The pump beam was scanned at 250 nm/pixel with 440 μW incident power at 640 nm.
Figure 15B:
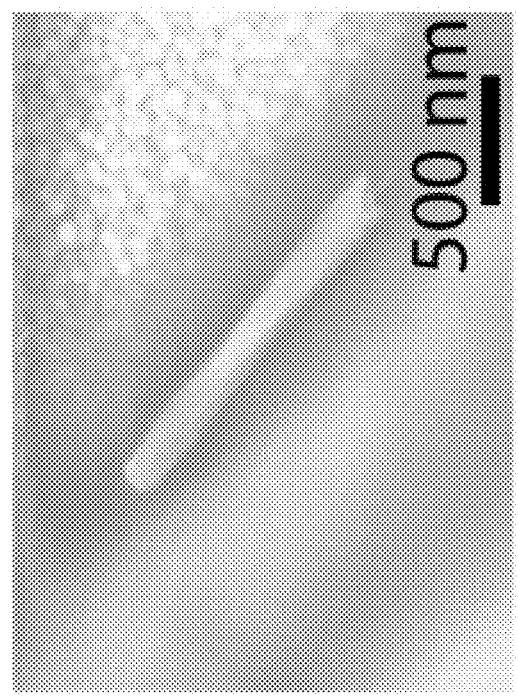
FIG. 15B shows a scanning electron micrograph.
Figure 15C:
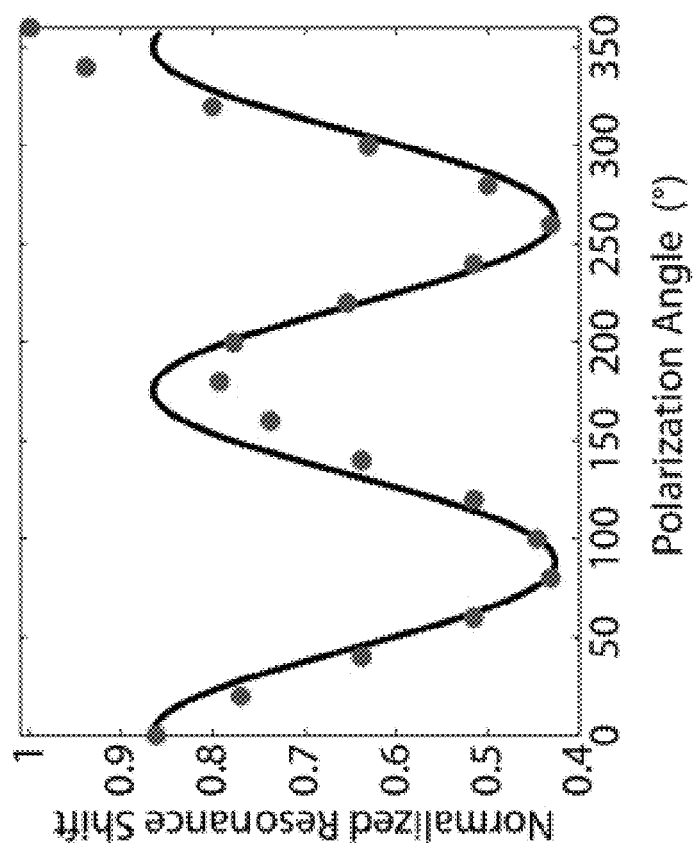
FIG. 15C shows the polarization dependence of photothermally-induced resonance shift.
Figure 15D:
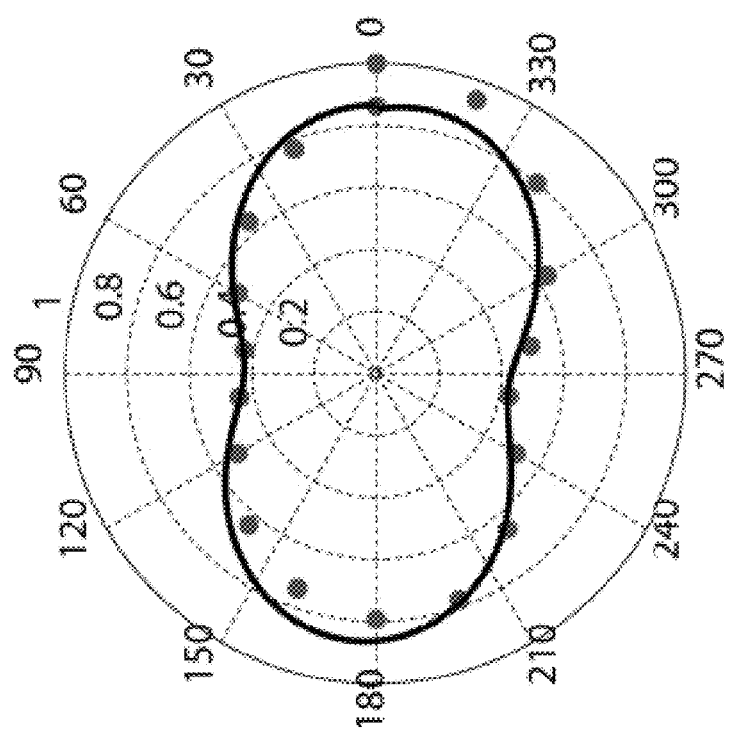
FIG. 15D shows the polarization dependence plotted in polar coordinates.

Photothermal images at variable resolution were taken by scanning the pump beam across the top surface of the resonator. Wide-area maps (50 μm×50 μm) at low resolution (2 μm/pixel) were used to locate individual absorbers. High-resolution maps (3 μm×3 μm at 250 nm/pixel) were taken to define the shape of the nanotube. One high-resolution map is shown in FIG. 14. These maps highlight the utility of using a whispering gallery mode-coupled probe beam while performing excitation with a scanning free-space pump beam. At every pixel the resonance wavelength was measured with the pump beam off and on, allowing for background subtraction, and five successive scans were averaged at each pixel. Scanning Electron Micrographs (SEMs) taken before and after photothermal experiments confirmed that the nanotubes were not significantly altered by the measurement and allowed correlation between the observed photothermal map and the physical dimensions, as described below with respect to FIGS. 15A-D.

MWCNTs (Sigma, >90% carbon basis) were dissolved in N-methyl pyrrolidone (Sigma) with ultrasonication at a concentration of 60 μg/mL without further purification and deposited onto resonator wafer chips by spincoating. Microresonators were plasma activated immediately prior to spincoating ($O_2$ plasma, 250 W, 5 min) to enhance adhesion. High Q factors were largely maintained (Q>2×10$^6$) after nanotube deposition (Q~10$^7$ pre-deposition). Nanotubes typically stuck to the inside of the silica rim during deposition (FIG. 15B) and were able to substantially thermally influence the propagating mode after photoexcitation. On the other hand, the nanotubes did not strongly influence the mode via direct absorption, as confirmed by the small reduction in Q and described further below. Both coarse and high-resolution photothermal maps were acquired in 7 minutes, although the thermal equilibration time of the microresonator (~250 μs) allows for much faster acquisition. Multiple molecules or particles on a single resonator can be individually spatially selected and probed, allowing for faster throughput, though more dense surface coverage will ultimately compromise the resonator quality factor.

Photothermal images were obtained for many nanotubes, one of which is shown in FIG. 14. MWCNTs were observed to be up to several microns in length but appeared with a diffraction-limited thickness, consistent with their high aspect ratio. Very high contrast was observed against the background (e.g. a Signal-to-Noise=425 and Signal-to-Background=36 were exhibited by one nanotube.) FIGS. 15A-D show a case study of a MWCNT including a photothermal map (A), a SEM image (B), as well as polarization dependence of the nanotube (C,D). Similar results were obtained for other nanotubes. The photothermal images matched the SEM images, including photothermal hotspots corresponding to the carbon-rich globules surrounding residual catalyst evident in nanotubes.

To calibrate the photothermal technique, the absorption cross-section was determined on a per-atom basis to account for the variation in size between nanotubes (Table 1). The absorption cross-section of nanotubes is a critical parameter for understanding their optical and device parameters. Table 1 lists the relevant parameters for four MWCNTs I-IV. (MWCNT I corresponds to the nanotube of FIGS. 15A-D.) The measured resonance shift, physical dimensions, and polarization extinction ratio were directly measured via photothermal absorption or SEM. The dissipated thermal power was calculated using finite-element simulations. The carbon fraction absorbing ($\beta$) and the per-atom absorption cross-section were calculated by analyzing the combined results of measurements and simulation.

TABLE 1

Parameters for Photothermal Measurement of MWCNTs

| | Resonance Shift (pm) | Diameter (μm) | Length (μm) | Dissipated thermal power (μW) | Carbon fraction absorbing, $\beta$ (%) | Per-atom absorption cross-section ($1 \times 10^{-18}$ cm$^2$/atom) | Polarization extinction ratio |
|---|---|---|---|---|---|---|---|
| I | 13.5 | 0.104 | 1.41 | 88 | 33.0 | 2.7 | 2.0:1 |
| II | 14.1 | 0.111 | 1.71 | 92 | 27.2 | 2.5 | 2.3:1 |
| III | 24.0 | 0.157 | 4.04 | 163 | 11.5 | 2.3 | 1.8:1 |
| IV | 16.6 | 0.154 | 2.99 | 111 | 15.4 | 1.6 | 1.6:1 |

All cross-section measurements were performed on regions of MWCNTs that were distant from any residual catalyst particles to avoid their influence on the calculation. Calculation of the absorption cross-section requires knowledge of the amount of light absorbed by the target, which can be determined from the magnitude of heat released. The heat dissipated can be calculated from the measured resonance wavelength shift of the microresonator. However, the relationship between the heat dissipated and the photothermal shift is a function of the position of the nanotube along the microresonator, which was determined from the SEM images. Then, finite element simulations were performed using the COMSOL Multiphysics package to calculate the temperature elevation at every point in the mode volume as a result of a nanoscopic heat source. The same approach was shown to correctly model the resonance shift of the microresonator in the absence of absorbing nano-objects as a result of the absorption from the silicon substrate as discussed in Example 1. The temperature along the rim of the microresonator was measured in a series of 2D slices at regular azimuthal spacing (5°). Using the literature value for the thermo-optic coefficient, the shifted refractive index was calculated at each point. (See, Leviton, D. B.; Frey, B. J. Temperature-dependent absolute refractive index measurements of synthetic fused silica. *Proc. SPIE-Int. Soc. Opt. Eng.* 2006, 6273, 62732K.) The shift in the refractive index was then weighted by the relative intensity ($|E|^2$) of the propagating mode. The total resonance shift of the toroid was calculated by averaging the resonance shift contribution from each slice.

The dissipated thermal power was then determined by matching the observed resonance shift. The pump intensity was easily determined from the optical pump power and the spot size. Finally, the known atom density and physical dimensions of the tube were used to extract the absorption cross-section per carbon atom, as summarized in the equation below, $$\sigma_{abs} = \frac{P_{thermal}}{P_{optical}} * \frac{1}{(1-\varphi_{lumin})} * \left[\pi * \left(\frac{w_0}{2}\right)^2\right] * \frac{M}{\pi * \left(\frac{d}{2}\right)^2 * L * \rho * N_a} * \beta$$

where $\sigma_{abs}$ is the absorption cross-section per carbon atom, $P_{thermal}$ the heat dissipated, $P_{optical}$ the pump beam power (440 µW), $\phi_{lumin}$ is the quantum yield for luminescence (0 for MWCNT), $w_0$ the $1/e^2$ beam diameter (780 nm), d and L are nanotube diameter and length respectively, $\rho$ is the density (1.75 g/cm$^3$), $N_a$ is Avogadro's number, M the molar mass (12.01 g/mole carbon), and $\beta$ the fraction of atoms in the nanotube excited by the pump beam. $\beta$ was calculated by taking an overlap integral between the measured spot size of the pump laser and the physical dimensions of the nanotube as measured by SEM. This correction was necessary because the spot size is the same order of magnitude as the diameter (100-170 nm) and length (1000-4000 nm) of the nanotubes. This procedure ultimately yielded a value of 2.3+/−0.5× $10^{-18}$ cm$^2$/C.

MWCNTs of the size (>100 nm diameter) studied in this example should have a per-atom optical absorption cross-section approaching that of bulk graphite due to the MWCNTs' relatively gentle curvature. Reported per-atom cross-sections of graphite range from 2.5-2.8×10$^{-18}$ cm$^2$/C, in excellent agreement with the results of this example. (See, Djurisic, A. B.; Li, E. H. Optical properties of graphite. *J. Appl. Phys.* 1999, 85, 7404-7410; Stagg, B. J.; Charalampopoulos, T. T. Refractive-Indexes of Pyrolytic-Graphite, Amorphous-Carbon, and Flame Soot in the Temperature-Range 25° C. to 600° C. *Combust. Flame* 1993, 94, 381-396; Greenawa; Harbeke, G.; Bassani, F.; Tosatti, E. Anisotropy of Optical Constants and Band Structure of Graphite. *Phys. Rev.* 1969, 178, 1340-1348 and Wang, X. F.; Chen, Y. P.; Nolte, D. D. Strong anomalous optical dispersion of graphene: complex refractive index measured by Picometrology. *Opt. Express* 2008, 16, 22105-22112.) The absorption cross-section of MWCNTs has been roughly estimated by dividing the bulk absorption of a MWCNT sample by the carbon atom density at 3.4×10$^{-18}$ cm$^2$/C. It is believed this example provides the first per-atom absorption cross-section of MWCNTs made on individual nanotubes.

Polarization dependence of the photothermal signal was investigated, as shown in FIG. 15 C, D. Angular dependence clearly follows a sin$^2\theta$ dependence, with the maximum photothermal shift observed with the pump beam polarized parallel to the long axis of the nanotube. The contrast ratio between parallel and perpendicular polarization was approximately 2:1.

This example demonstrates the use of the photothermal technique for single-molecule photothermal microscopy and spectroscopy. Extrapolation to the absorption cross-section of a single chromophore (~1×10$^{-16}$ cm$^2$) from a nanotube suggests a molecular shift of 2.1 fm, a value significantly greater than the smallest detectable resonance shifts in toroidal microresonators. This is also consistent with the calculations discussed in Example 2.

To summarize, this example presents a new method for measuring optical absorption at the single particle level by combining the sensitivity of ultra-high Q optical microresonators with the spectral specificity of photothermal absorption. The polarization-dependent per-atom absorption cross-section of individual MWCNTs was successfully measured by mapping out the spatially-resolved optical absorption and heat dissipation. The ultimate limit of sensitivity was calculated to be several orders of magnitude smaller, allowing for detection of absorption by non-luminescent single molecules under ambient conditions. This technique places few requirements on the target system's properties and does not require multiple objectives or a transparent substrate. Photothermal approaches are also immune to contributions from scattered light and, when combined with direct absorption approaches, provide complementary information in regard to characterizing the flow of energy in nano-objects. Further, toroidal microresonators are compatible with water and may be used to study chemical or biological reactions in real time. The simple fixed-wavelength pump laser used in this example may be replaced with a tunable source to perform broadband visible absorption spectroscopy using toroidal microresonators. Extending spectroscopy of non-luminescent targets towards single molecules and smaller nano-objects provides a powerful new tool for investigating structure and dynamics at the nanoscale while also offering needed additional chemical information for label-free sensing.

Additional SEMs of nanotubes, analysis of the background and noise level, analysis of the pump beam and nanotube overlap integral, time-dependence and power-dependence testing of the COMSOL simulations, measured pump-power-dependence of the resonance shift, and testing of the effects of various simulation parameters on the calculated resonance shift were also performed (data not shown).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for single particle or single molecule spectroscopy comprising:
    (a) exposing the surface of an optical microcavity characterized by at least one resonance frequency to a sample such that a single particle or a single molecule from the sample adsorbs onto the surface of the microcavity;
    (b) evanescently coupling a probe laser beam into the microcavity, wherein the wavelength of the probe laser beam substantially matches the at least one resonance frequency;
    (c) illuminating the surface of the microcavity with a free space pump light beam and moving the focal spot of the free space pump light beam such that the focal spot of the free space pump light beam substantially overlaps with the single particle or the single molecule; and
    (d) detecting light from the probe laser beam,
    wherein the wavelength of the free space pump light beam is that which generates sufficient heat via energy absorbed by the single particle or the single molecule from the free space pump light beam to induce a shift in the at least one resonance frequency, thereby providing a change in an optical characteristic of the detected light from the probe laser beam.

2. The method of claim 1, wherein the wavelength of the free space pump light beam is substantially resonant with a transition in the single particle or the single molecule.

3. The method of claim 2, wherein the transition is an electronic transition.

4. The method of claim 1, wherein the wavelength of the free space pump light beam is substantially non-resonant with the resonance frequencies of the microcavity.

5. The method of claim 1, wherein the size of the focal spot is diffraction-limited.

6. The method of claim 1, wherein the intensity of the free space pump light beam is below the saturation intensity of the single particle or the single molecule.

7. The method of claim 1, wherein the microcavity is a whispering gallery mode optical microcavity.

8. The method of claim 7, wherein the microcavity is a toroid.

9. The method of claim 8, wherein the microcavity is substantially free of silicon and is not in thermal contact with silicon.

10. The method of claim 1, wherein the surface coverage of single particles or single molecules on the surface of the microcavity is such that there is no more than one single particle or one single molecule per an area having the size of the focal spot.

11. The method of claim 1, further comprising adjusting the wavelength of the probe laser beam via Pound-Drever-Hall stabilization such that it remains substantially matched to the at least one resonance frequency.

12. The method of claim 1, further comprising modulating the amplitude of the free space pump light beam at a selected frequency and extracting components from the detected light which are modulated at substantially the same frequency.

13. The method of claim 1, wherein the wavelength of the free space pump light beam is scanned over a range of wavelengths encompassing a wavelength which is resonant with an electronic transition of the single particle or the single molecule, and the detected light is detected as a function of the wavelength of the free space pump light beam.

14. The method of claim 1, wherein the wavelength of the free space pump light beam is substantially near an absorption maximum of an electronic transition of the single particle or the single molecule, and the detected light is detected for a period of time.

15. The method of claim 1, wherein the focal spot of the free space pump light beam substantially overlaps with the propagating mode in the microcavity.

16. An apparatus for single particle or single molecule spectroscopy, the apparatus comprising:
    (a) an optical microcavity characterized by at least one resonance frequency;
    (b) optical components configured to evanescently couple a probe laser beam into the microcavity;
    (c) optical components configured to illuminate the surface of the microcavity with a free space pump light beam and to move the focal spot of the free space pump light beam across the surface of the microcavity;
    (d) a detector configured to detect light from the probe laser beam; and
    (e) a Pound-Drever-Hall servo loop coupled to the probe laser beam, the loop configured to adjust the wavelength of the probe laser beam such that it remains substantially resonant with the microcavity,
    wherein the apparatus is configured to detect a change in an optical characteristic of the detected light due to a shift in the at least one resonance frequency induced by heat generated and transferred to the microcavity from a single particle or a single molecule in a sample adsorbed on the surface of the microcavity via energy absorbed by the single particle or the single molecule from the free space pump light beam.

17. The apparatus of claim 16, further comprising a lock-in amplification system coupled to the free space pump light beam, the system configured to modulate the amplitude of the free space pump light beam at a selected frequency and to extract components from the detected light which are modulated at substantially the same frequency.

18. The apparatus of claim 17, wherein the microcavity is a whispering gallery mode optical microcavity.

19. The apparatus of claim 18, wherein the microcavity is a toroid.

20. The apparatus of claim 19, wherein the microcavity is substantially free of silicon and is not in thermal contact with silicon.

* * * * *